US007384774B2

(12) United States Patent
Palese et al.

(10) Patent No.: US 7,384,774 B2
(45) Date of Patent: *Jun. 10, 2008

(54) HELPER-FREE RESCUE OF RECOMBINANT NEGATIVE STRAND RNA VIRUS

(75) Inventors: Peter Palese, Leonia, NJ (US); Adolfo Garcia-Sastre, New York, NY (US); George G Brownlee, Oxford (GB); Ervin Fodor, Oxford (GB)

(73) Assignee: Mount Sinai School of Medicine of New York University, New york, NY (US)

( * ) Notice: Subject to any disclaimer, the term of this patent is extended or adjusted under 35 U.S.C. 154(b) by 310 days.

This patent is subject to a terminal disclaimer.

(21) Appl. No.: 10/652,912

(22) Filed: Aug. 28, 2003

(65) Prior Publication Data

US 2004/0142003 A1    Jul. 22, 2004

Related U.S. Application Data

(60) Continuation of application No. 09/724,412, filed on Nov. 28, 2000, now Pat. No. 6,649,372, which is a division of application No. 09/616,527, filed on Jul. 14, 2000, now Pat. No. 6,544,785, and a continuation-in-part of application No. 09/152,845, filed on Sep. 14, 1998, now Pat. No. 6,146,642.

(60) Provisional application No. 60/143,645, filed on Jul. 14, 1999.

(51) Int. Cl.
*C12N 7/00*    (2006.01)
*A61K 39/145*    (2006.01)

(52) U.S. Cl. ............... 435/235.1; 435/69.1; 424/206.1

(58) Field of Classification Search ..................... None
See application file for complete search history.

(56) References Cited

U.S. PATENT DOCUMENTS

| | | | |
|---|---|---|---|
| 4,071,618 A | 1/1978 | Konobe et al. | |
| 4,659,569 A | 4/1987 | Mitsuhashi et al. | |
| 5,166,057 A | 11/1992 | Palese et al. | |
| 5,716,821 A | 2/1998 | Wertz et al. | |
| 5,789,229 A | 8/1998 | Wertz et al. | |
| 5,820,871 A | 10/1998 | Palese et al. | |
| 5,840,520 A | 11/1998 | Clarke et al. | |
| 5,854,037 A | 12/1998 | Palese et al. | |
| 6,033,886 A | 3/2000 | Conzelmann et al. | |
| 6,146,642 A * | 11/2000 | Garcia-Sastre et al. | 424/214.1 |
| 6,168,943 B1 | 1/2001 | Rose | |
| 6,544,785 B1 * | 4/2003 | Palese et al. | 435/325 |
| 6,649,372 B1 * | 11/2003 | Palese et al. | 435/69.1 |

FOREIGN PATENT DOCUMENTS

| | | |
|---|---|---|
| CA | 2118234 | 4/1993 |
| EP | 0 702 085 | 3/1996 |
| EP | 0 780 475 | 6/1997 |
| EP | 0 863 202 | 9/1998 |
| EP | 0 864 645 | 9/1998 |
| GB | 0279563 A2 * | 4/1988 |
| WO | WO 96/10632 | 4/1996 |
| WO | WO 96/34625 | 11/1996 |
| WO | WO 97/06270 | 2/1997 |
| WO | WO 97/12032 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 00/53786 | 9/2000 |
| WO | WO 00/60050 | 10/2000 |

OTHER PUBLICATIONS

Zhang et al. (1994) Biochemical and Biophysical Research Communications, 200(1):95-101.*
Drake, PNAS vol. 90, pp. 4171-4175 (1993).
Hoffmann et al., Vaccine, Vo. 20, pp. 3165-3170 (2002) (Abstract only).
Hoffmann and Webster J. Gen. Virol. vol. 81, pp. 2843-2847 (2000).
Nicolson et al., Vaccine, vol. 23, pp. 2943-2952 (2005).
Pekosz et al., PNAS, vol. 96, pp. 8804-8806 (1999).
Steinhauer and Skehel, Ann. Rev. Genet., vol. 36, pp. 305-332 (2002).
Suarez et al., J. Virology, vol. 66, pp. 2491-2494 (1992).
Tannock et al., Archives of Virology, vol. 140, pp. 201-209 (1995).
Banerjee and Barik, 1992, "Gene expression of vesicular stomatitis virus genome RNA", Virology. 188(2):417-28.
Baron and Barrett, 1997, "Rescue of Rinderpest Virus from Cloned cDNA". J. Virol. 71:1265-1271.
Beare et al., 1975, "Trials in Man with Live Recombinants Made from A/PR/8/34 (HO N1) and Wild H3 N2 Influenza Viruses", Lancet 2(7938)729-732.

(Continued)

*Primary Examiner*—Stacy B Chen
(74) *Attorney, Agent, or Firm*—Elliot M. Olstein; Alan J. Grant

(57) ABSTRACT

The present invention relates methods of generating infectious negative-strand virus in host cells by an entirely vector-based system without the aid of a helper virus. In particular, the present invention relates methods of generating infectious recombinant negative-strand RNA viruses intracellularly in the absence of helper virus from expression vectors comprising cDNAs encoding the viral proteins necessary to form ribonucleoprotein complexes (RNPs) and expression vectors comprising cDNA for genomic viral RNA(s) (vRNAs) or the corresponding cRNA(s). The present invention also relates to methods of generating infectious recombinant negative-strand RNA viruses which have mutations in viral genes and/or which express, package and/or present peptides or polypeptides encoded by heterologous nucleic acid sequences. The present invention further relates the use of the recombinant negative-strand RNA viruses or chimeric negative-strand RNA viruses of the invention in vaccine formulations and pharmaceutical compositions.

24 Claims, 9 Drawing Sheets

OTHER PUBLICATIONS

Figure 1:
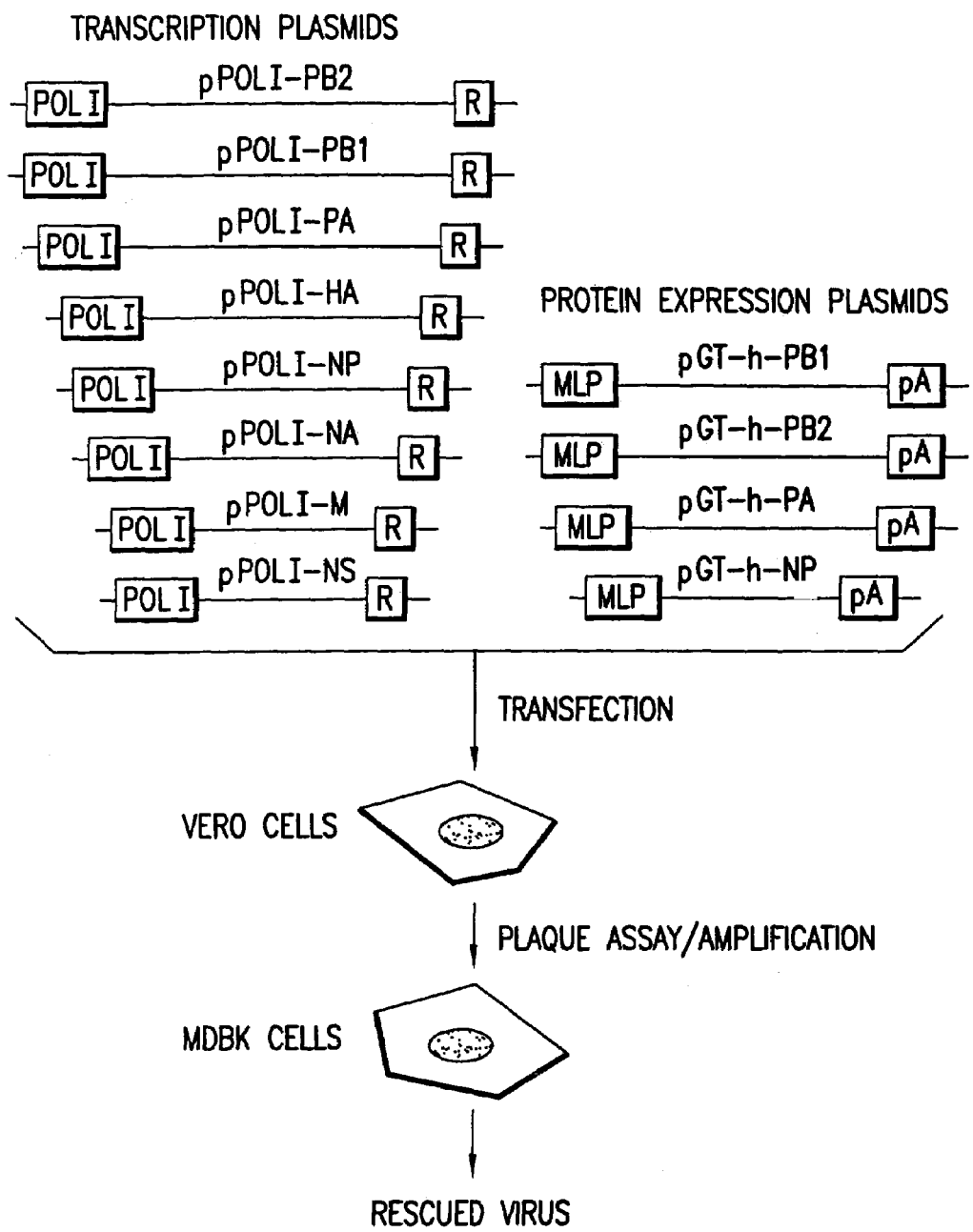

Boyer et al., 1995, "Infectious transcripts and cDNA clones of RNA viruses", Virology. 198(2):415-26.

Brigden and Elliott, 1996, "Rescue of a Segmented Negative-Strand RNA Virus Entirely from Cloned Complementary DNAs", Proc. Natl. Acad. Sci. USA 93:15400-15404.

Buchholz et al., 1999, "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter", J. Virol. 73:251-259.

Bukreyev et al., "Recovery of infectious respiratory syncytial virus expressing an additional, foreign gene", J Virol. 70(10):6634-41. 1996.

Castrucci et al., 1995, "Reverse genetics system for generation of an influenza A virus mutant containing a deletion of the carboxyl-terminal residue of M2 protein", J Virol. 69(5):2725-8.

Chen et al., 1999, "Influenza A virus NS1 protein targets poly(A)-binding protein II of the cellular 3'-end processing machinery", EMBO 18: 2273-2283.

Clarke et al., 2000, "Rescue of mumps virus from cDNAJ", J Virol. 74(10):4831-8.

Collins et al., 1991, "Rescue of Synthetic Analogs of Respiratory Syncytial Virus Genomic RNA and Effect of Truncations and Mutations on the Expression of a Foreign Reporter Gene", Proc. Natl. Acad. Sci. USA 88:9663-9667.

Collins et al., 1995, "Production of infectious human respiratory syncytial virus from cloned cDNA confirms an essential role for the transcription elongation factor from the 5' proximal open reading frame of the M 2 RNA in gene expression and provides a capability for vaccine development", J. Virol. 71:1265-1271.

Collins et al., 1996, "Parainfluenza Viruses", Fields Virology, Lippincott-Raven Publishers, Phila., pp. 1205-1242.

Conzelmann et al., 1996, "Genetic manipulation of non-segmented negative-strand RNA viruses", J Gen Virol. 77 (Pt 3): 381-9.

Conzelmann et al., 1998, "Nonsegmented negative-strand RNA viruses: genetics and manipulation of viral genomes", Annu Rev Genet. 32:123-62.

Conzelmann et al., 1996, "Genetic engineering of animal RNA viruses", Trends Microbiol. 4(10):386-93.

Conzelmann et al., 1994, "Rescue of synthetic genomic RNA analogs of rabies virus by plasmid-encoded proteins", J Virol. 68(2):713-9.

De la Luna et al., 1993, "Influenza virus naked RNA can be expressed upon transfection into cells co-expressing the three subunits of the polymerase and the nucleoprotein from simian virus 40 recombinant viruses", J Gen Virol. 74 ( Pt 3):535-9.

De la Luna et al., 1995, "Influenza virus NS1 Protein Enhances the Rate of Translation Initiation of Viral mRNAs", J. of Virol. 69:2427-2433.

De and Banerjee, 1985, "Requirements and Functions of Vesicular Stomatitis Virus L and NS Proteins in the Transcription Process in vitro", Biochem. Biophys. Res. Commun. 126:40-49.

De and Banerjee, 1992, "Rescue of synthetic analogs of genome RNA of human parainfluenza virus type 3", Virology. 96(1):344-8.

De and Banerjee, 1994, "Reverse genetics of negative strand RNA viruses", Indian J Biochem Biophys. 31(5):367-76.

Dimock et al., 1993, "Rescue of synthetic analogs of genomic RNA and replicative-intermediate RNA of human parainfluenza virus type 3.", J Virol. 67(5):2772-8.

Dreher et al., 1984, "Mutant Viral RNAs Synthesized in vitro Show Altered Aminoacylation and Replicase Template Activities", Nature 311:171-175.

Dreher and Hall, 1988, "Mutational Analysis of the Sequence and Structural Requirements in Brome Mosaic Virus RNA for Minus Strand Promoter Activity", J. Mol. Biol. 201:31-40.

Dunn et al., 1995, "Transcription of a recombinant bunyavirus RNA template by transiently expressed bunyavirus proteins", Virology. 211(1):133-43.

Durbin et al., 1997, "Recovery of Infectious Human Parainfluenza Virus Type 3 from cDNA", Virol. 235:323-332.

Elliot et al., 1997, Abstract # 96 10th International conference on Negative Strand Viruses.

Elliott et al., 1991, "Some highlights of virus research in 1990", J Gen Virol.72 ( Pt 8):1761-79. Review. No abstract available.

Emerson and Yu, 1975, "Both NS and L Proteins are Required for in vitro RNA Synthesis by Vesicular Stomatitis Virus", J. Virol 15:1348-1356.

Enami and Palese, 1991, "High-Efficiency Formation of Influenza Virus Transfectants", J. Virol. 65:2711-2713.

Enami et al., 1991, "An influenza virus containing nine different RNA segments", Virology. 185(1):291-8.

Fahey and Schooley, 1992, "Status of Immune-Based Therapies in HIV Infection and AIDS", Clin. Exp. Immunol. 88:1-5.

Fodor et al., 1999, "Rescue of Influenza A Virus from Recombinant DNA", J. Virol. 73:9679-9682.

Fortes et al., 1994, "Influenza virus NS1 protein inhibits pre-mRNA splicing and blocks mRNA nucleocytoplasmic transport", EMBO 13: 704-712.

Garcia-Sastre A, Palese P, 1993, "Genetic manipulation of negative-strand RNA virus genomes", Annu Rev Microbiol.; 47:765-90.

Garcin et al., 1995, "A highly recombinogenic system for the recovery of infectious sendai paramyxovirus from cDNA: generation of a novel copy-back nondefective interfering virus", EMBO J. 14: 6087-6094.

Goto et at., 1997, "Mutations Affecting the Sensitivity of the Influenza Virus Neuraminidase to 4-Guanidino-2,4-Dideoxy-2,3-Dehydro-$N$-Acetylneuraminic Acid", Virol. 238:265-272.

Grosfeld et al., 1995, RNA replication by respiratory syncytial virus (RSV) is directed by the N, P, and L proteins; transcription also occurs under these conditions but requires RSV superinfection for efficient synthesis of full-length mRNA. J Virol. 69(9):5677-86.

Hatada and Fukuda, 1992, "Binding of influenza A virus NS1 protein to dsRNA in vitro", J. of Gen. Virol. 73: 3325-3329.

He et al., 1997, "Recovery of Infectious SV5 from Cloned DNA and Expression of a Foreign Gene", Virol. 237:249-260.

Hoffman and Banerjee, 1997, "An Infectious Clone of a Human Parainfluenza Virus Type 3", J. Virol. 71:4272-4277.

Huang et al., 1990, "Determination of influenza virus proteins required for genome replication", J Virol. 64(11):5669-73.

Kaplan et al., 1985, "In vitro Synthesis of Infectious Poliovirus RNA", Proc. Natl. Acad. Sci. USA 82:8424-8428.

Katinger et al., 1997, "Attenuated Influenza Virus as a Vector for Mucosal Immunization against HIV-1", Vaccines 315-319.

Kato et al., 1996, "Initiation of Sendai Virus Multiplication from Transfected cDNA or RNA with Negative or Positive Sense", Genes Cells 1:569-579.

Kimura et al., 1993, "An in vivo study of the replication origin in the influenza virus complementary RNA", J Biochem (Tokyo) 113(1):88-92.

Kimura et al., 1992, "Transcription of a recombinant influenza virus RNA in cells that can express the influenza virus RNA polymerase and nucleoprotein genes", J Gen Virol. 73 ( Pt 6):1321-8.

Kobayashi, 1992, Reconstitution of influenza virus RNA polymerase from three subunits expressed using recombinant baculovirus system. Virus Res. 22(3):235-45.

Konarska et al., 1990, "Structure of RNAs replicated by the DNA-dependent T7 RNA polymerase", Cell. 63(3):609-18.

Krystal et al., 1986, "Expression of the Three Influenza Virus Polymerase Proteins in a Single Cell Allows Growth Complementation of Viral Mutants", Proc. Natl. Acad. Sci. USA 83:2709-2713.

Kunkel, 1985, "Rapid and Efficient Site-Specific Mutagenesis without Phenotypic Selection", Proc. Natl. Acad. Sci. USA 82:488-492.

Lamb et al., 1996, Fundamental Virology 3rd ed. Chapters 20 and 21.

Lawson et al., 1995, "Recombinant vesicular stomatitis viruses from DNA", Proc Natl Acad Sci USA.92(10):4477-81.

Levis et al., 1986, "Deletion Mapping of Sindbis Virus DI RNAs Derived from cDNAs Defines the Sequences Essential for Replication and Packaging", Cell 44:137-145.

Luyties et al., 1989, "Amplification, Expression, and Packaging of a Foreign Gene by Influenza Virus", Cell 59:1107-1113.

Mena et al., 1994, "Synthesis of biologically active influenza virus core proteins using a vaccinia virus-T7 RNA polymerase expression system", J Gen Virol. 75 (Pt 8):2109-14.

Mena et al., 1996, "Rescue of a Synthetic Chloramphenicol Acetyltransferase RNA into Influenza Virus-Like Particles Obtained from Recombinant Plasmids", J. Virol. 70: 5016-5024.

Moyer et al., 1995, "Assembly and transcription of synthetic vesicular stomatitis virus nucleocapsids", J Virol. 65(5):2170-8.

Muster et al., 1991, "An influenza A virus containing influenza B virus 5' and 3' noncoding regions on the neuraminidase gene is attenuated in mice:", Proc Natl Acad Sci USA.88(12):5177-81.

Naito and Ishihama, 1976, "Function and Structure of RNA Polymerase from Vesicular Stomatitis Virus", J. Biol. Chem. 251:4307-4314.

Nara et al., 1987, "Simple, Rapid, Quantitative, Syncytium-Forming Microassay for the Detection of Human Immunodeficiency Virus Neutralizing Antibody", AIDS Res. Hum. Retroviruses 3:283-302.

Nemeroff et al., 1998, "Influenza Virus NS1 Protein Interacts with the Cellular 30 kDa Subunit of CPSF and Inhibits 3' End Formation of Cellular Pre-mRNAs", Mol. Cell 1:991-1000.

Neumann et al., 1994, "RNA Polymerase I-Mediated Expression of Influenza Viral RNA Molecules", Virol. 202:477-479.

Neumann et al., 1999, "Generation of Influenza A Viruses Entirely from Cloned cDNAs", Proc. Natl. Acad. Sci. USA 96:9345-9350.

Palese et al., 1996, "Negative-Strand RNA Viruses: Genetic Engineering and Applications", Proc. Natl. Acad. Sci. USA 93:11354-11358.

Park et al., 1991, "Rescue of a Foreign Gene by Sendai Virus", Proc. Natl. Acad. Sci. USA 88:5537-5541.

Pattnaik et al., 1991, "Cells that express all five proteins of vesicular stomatitis virus from cloned cDNAs support replication, assembly, and budding of defective interfering particles", Proc Natl Acad Sci USA. 88(4):1379-83.

Peeters et al., 1999, "Rescue of Newcastle Disease Virus from Cloned cDNA: Evidence that Cleavability of the Fusion Protein Is a Major Determinant for Virulence", J. Virol. 73:5001-5009.

Pekosz et al., 1999, "Reverse genetics of negative-strand RNA viruses: closing the circle", Proc Natl Acad Sci USA. 96(16):8804-6.

Percy et al., 1994, "Expression of a foreign protein by influenza A virus", J Virol. 68(7):4486-92.

Pleschka et al., 1996, "A Plasmid-Based Reverse Genetics System for Influenza A Virus", J. Virol. 70:4188-4192.

Qiu et al., 1995, "The influenza virus NS1 protein binds to a specific region in human U6 snRNA and inhibits U6-U2 and U6-U4 snRNA interactions during splicing", RNA Society 1:304-16.

Qiu et al., 1994, "The influenza virus NS1 protein is a poly(A)-binding protein that inhibits nuclear export of mRNAs containing poly(A)", J Virol. 68(4):2425-32.

Racaniello et al., 1981, "Cloned Poliovirus Complementary DNA is Infectious in Mammalian Cells", Science 214:916-919.

Radecke et al., 1997, "Reverse Genetics Meets the Nonsegmented Negative-Strand RNA Viruses", Rev Med Virol. 7(1):49-63.

Radecke et al., 1995, "Rescue of measles viruses from cloned DNA", EMBO J. 14(23):5573-84.

Roberts and Rose, 1998, "Recovery of Negative-Strand RNA Viruses from Plasmid DNAs: a Positive Approach Revitalizes a Negative Field", Virol. 247:1-6.

Rose et al., 1996, "Positive strands to the rescue again: a segmented negative-strand RNA virus derived from cloned cDNAs", Proc Natl Acad Sci USA. 93(26):14998-5000.

Schlesinqer et al., 1995, "RNA viruses as vectors for the expression of heterologous proteins", Mol Biotechnol. 3(2):155-65.

Schnell et al., 1994, "Infectious Rabies Viruses from Cloned cDNA", EMBO J. 13:4195-4203.

Seong et al., 1992, A new method for reconstituting influenza polymerase and RNA in vitro: a study of the promoter elements for cRNA and vRNA synthesis in vitro and viral rescue in vivo. Virology. 186(1):247-60.

Sidhu et al., 1995, "Rescue of synthetic measles virus minireplicons: measles genomic termini direct efficient expression and propagation of a reporter gene", Virology. 208(2):800-7.

Subbarao et al., 1995, "Sequential addition of temperature-sensitive missense mutations into the PB2 gene of influenza A transfectant viruses can effect and increase in temperature sensitivity and attenuation and permits the rational design of a genetically engineered live influenza A virus vaccine", J Virol. 69(10):5969-77.

Szewczyk et al., 1988, "Purification, Thioredoxin Renaturation, and Reconstituted Activity of the Three Subunits of the Influenza A Virus RNA Polymerase", Proc. Natl. Acad. Sci. USA 85:7907-7911.

Taylor et al., 1990, "Newcastle Disease Virus Fusion Protein Expressed in a Fowlpox Virus Recombinant Confers Protection in Chickens", J. Virol. 64:1441-1450.

Ward et al., 1988, "Direct Measurement of the Poliovirus RNA Polymerase Error Frequency In Vitro", J. Virol. 62:558-562.

Whelan et al., 1995, "Efficient recovery of infectious vesicular stomatitis virus entirely from cDNA clones", Proc .Natl .Acad. Sci. USA 92: 8388-8392.

Yu et al., 1995, "Functional cDNA clones of the human respiratory syncytial (RS) virus N, P, and L proteins support replication of RS virus genomic RNA analogs and define minimal trans-acting requirements for RNA replication", J Virol. 69(4):2412-9.

Yusoff et al., 1987, "Nucleotide Sequence Analysis of the L Gene of Newcastle Disease Virus: Homologies with Sendi and Vesicular Stomatitis Viruses" Nucleic Acids Res. 15:3961-76.

Zaghouani et al., 1991, "Induction of antibodies to the envelope protein of the human immunodeficiency virus by immunization with monoclonal anti-idiotypes", Proc. Natl. Acad. Sci. USA 88:5645-5649.

Zaghouani et al., 1992, "Cells Expressing an H Chain Ig Gene Carrying a Viral T Cell Epitope Are Lysed by Specific Cytolytic T Cells", J. Immunol. 148:3604-3609.

Zhang and Air, 1994, "Expression of Functional Influenza Virus a Polymerase Proteins and Template from Cloned cDNAs in Recombinant Vaccinia Virus Infected Cells", Biochem. Biophys. Res. Commun. 200:95-101.

Zobel et al., 1993, "RNA polymerase I catalysed transcription of insert viral cDNA", Nucleic Acids Res. 21(16):3607-14.

Enami et al., 1990, "Introduction of Site Specific Mutations into the Genome of Influenza Virus", Proc Natl Acad Sci USA 87:3802-3805.

Hoffman et al., 2000, "Ambisense approach for the generation of influenza A virus: vRNA and mRNA synthesis from one template", Virology 267:310-7.

Yamanaka et al., In vivo analysis of the promoter structure of the influenza virus RNA genome using a transfection system with an engineered RnA, PNAS USA, 1991, 88(12) :5369-5373.

* cited by examiner

5'ACCAAACAGAGAAUCCGUAAGGUACGUUAAAAAGCGAAGGAGCAAUUGAAGUCGCACGGG
UAGAAGGUGUGAAUCUCGAGUGCGAGCCCGAAGCACAAACUCGAGAAAGCCUUCUACCAAC-
------------------CAT gene (667 nt)------------------cuuaa
CGACAAUCACAUAUUAAUAGGCUCCUUUUCUGGCCAAUUGUAUCCUUGUUGAUUUAAUCAUA
CUAUGUUAGAAAAAAGUUGAACUCCGACUCCUUAGGACUCGAACUCGAACUCAAAUAAAUGU
CUUAGAAAAAGAUUGCGCACAGUUAUUCUUGAGUGUAGUCUUGUCAUUCACCAAAUCUUUGU
UUGGU-3'

FIG.4

1 TGGTTTGTCTCTTAGGCATTCCATGCAATTTTTCGCTTCCTCGTTAACTT 50
1 TGGTTTGTCTCTTAGGCATTCCATGCTATTTTCCGCTTCCTCGTTAACTT 50
  *********************** * ****************

51 CA---TGCCCATCTTCC 64
51 CAGCATGCCCATCTTCC 67
      ***********

FIG.6

SEQUENCE LISTING

<160> NUMBER OF SEQ ID NOS: 5

<210> SEQ ID NO 1
<211> LENGTH: 121
<212> TYPE: RNA
<213> ORGANISM: Newcastle disease virus

<400> SEQUENCE: 1

```
accaaacaga gaauccguaa gguacguuaa aaagcgaagg agcaauugaa gucgcacggg      60
uagaaggugu gaaucucgag ugcgagcccg aagcacaaac ucgagaaagc cuucuaccaa     120
c                                                                    121

<210> SEQ ID NO 2
<211> LENGTH: 196
<212> TYPE: RNA
<213> ORGANISM: Newcastle disease virus

<400> SEQUENCE: 2
cuuaacgaca aucacauauu aauaggcucc uuuucuggcc aauuguaucc uuguugauuu      60
aaucauacua uguuagaaaa aaguugaacu ccgacuccuu aggacucgaa cucgaacuca     120
aauaaauguc uuagaaaaag auugcgcaca guuauucuug aguguagucu ugucauucac     180
caaaucuuug uuuggu                                                    196

<210> SEQ ID NO 3
<211> LENGTH: 64
<212> TYPE: DNA
<213> ORGANISM: Newcastle disease virus

<400> SEQUENCE: 3
tggtttgtct cttaggcatt ccatgcaatt tttcgcttcc tcgttaactt catgcccatc      60
ttcc                                                                  64

<210> SEQ ID NO 4
<211> LENGTH: 67
<212> TYPE: DNA
<213> ORGANISM: Artificial Sequence
<220> FEATURE:
<223> OTHER INFORMATION: Description of Artificial Sequence:
                        Illustrative parainfluenza comparison
                        sequence

<400> SEQUENCE: 4
tggtttgtct cttaggcatt ccatgctatt ttccgcttcc tcgttaactt cagcatgccc      60
atcttcc                                                               67

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
                        linker sequence

<400> SEQUENCE: 5
agaagagcca gatctggctc ttcc                                            24
```

HELPER-FREE RESCUE OF RECOMBINANT NEGATIVE STRAND RNA VIRUS

This application is a continuation-in-part of application Serial No. 60/143,645, filed Jul. 14, 1999 and application Ser. No. 09/152,845, filed Sep. 14, 1998, each of which is incorporated herein by reference in its entirety.

1. INTRODUCTION

The present invention relates to methods of generating infectious recombinant negative-strand RNA viruses in mammalian cells from expression vectors in the absence of helper virus. The present invention also relates to methods of generating infectious recombinant negative-strand RNA viruses which have mutations in viral genes and/or which express, package and/or present peptides or polypeptides encoded by heterologous nucleic acid sequences. The present invention further relates the use of the recombinant negative-strand RNA viruses or chimeric negative-strand RNA viruses of the invention in vaccine formulations and pharmaceutical compositions.

2. BACKGROUND OF THE INVENTION

A number of DNA viruses have been genetically engineered to direct the expression of heterologous proteins in host cell systems (e.g., vaccinia virus, baculovirus, etc.). Recently, similar advances have been made with positive-strand RNA viruses (e.g., poliovirus). The expression products of these constructs, i.e., the heterologous gene product or the chimeric virus which expresses the heterologous gene product, are thought to be potentially useful in vaccine formulations (either subunit or whole virus vaccines). One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia, in that multiple vaccinations will generate host-resistance to the strain so that the inoculated virus cannot infect the host. Inoculation of a resistant individual with chimeric vaccinia will, therefore, not induce immune stimulation.

By contrast, the negative-strand RNA viruses, would be attractive candidates for constructing chimeric viruses for use in vaccines. The negative-strand RNA virus, influenza, for example is desirable because its wide genetic variability allows for the construction of a vast repertoire of vaccine formulations which stimulate immunity without risk of developing a tolerance.

2.1. ENGINEERING NEGATIVE STRAND RNA VIRUSES

The RNA-directed RNA polymerases of animal viruses have been extensively studied with regard to many aspects of protein structure and reaction conditions. However, the elements of the template RNA which promote optimal expression by the polymerase could only be studied by inference using existing viral RNA sequences. This promoter analysis is of interest since it is unknown how a viral polymerase recognizes specific viral RNAs from among the many host-encoded RNAs found in an infected cell.

Animal viruses containing plus-sense genome RNA can be replicated when plasmid-derived RNA is introduced into cells by transfection (for example, Racaniello et al., 1981, Science 214:916-919; and Levis, et al., 1986, Cell 44:137-145). In the case of poliovirus, the purified polymerase will replicate a genome RNA in in vitro reactions and when this preparation is transfected into cells it is infectious (Kaplan, et al., 1985, Proc. Natl. Acad. Sci. USA 82:8424-8428). However, the template elements which serve as transcription promoter for the poliovirus-encoded polymerase are unknown since even RNA homopolymers can be copied (Ward, et al., 1988, J. Virol. 62:558-562). SP6 transcripts have also been used to produce model defective interfering (DI) RNAs for the Sindbis viral genome. When the RNA is introduced into infected cells, it is replicated and packaged. The RNA sequences which were responsible for both recognition by the Sindbis viral polymerase and packaging of the genome into virus particles were shown to be within 162 nucleotides (nt) of the 5' terminus and 19 nt of the 3' terminus of the genome (Levis, et al., 1986, Cell 44:137-145). In the case of brome mosaic virus (BMV), a positive strand RNA plant virus, SP6 transcripts have been used to identify the promoter as a 134 nt tRNA-like 3' terminus (Dreher, and Hall, 1988, J. Mol. Biol. 201:31-40). Polymerase recognition and synthesis were shown to be dependent on both sequence and secondary structural features (Dreher, et al., 1984, Nature 311:171-175).

The negative-sense RNA viruses have been refractory to study of the sequence requirements of the replicase. The purified polymerase of vesicular stomatitis virus is only active in transcription when virus-derived ribonucleoprotein complexes (RNPs) are included as template (De and Banerjee, 1985, Biochem. Biophys. Res. Commun. 126:40-49; Emerson and Yu, 1975, J. Virol. 15:1348-1356; Naito, and Ishihama, 1976, J. Biol. Chem. 251:4307-4314). With regard to influenza viruses, it was reported that naked RNA purified from virus was used to reconstitute RNPs. The viral nucleocapsid and polymerase proteins were gel-purified and renatured on the viral RNA using thioredoxin (Szewczyk, et al., 1988, Proc. Natl. Acad. Sci. USA 85:7907-7911). However, these authors did not show that the activity of the preparation was specific for influenza viral RNA, nor did they analyze the signals which promote transcription.

Only recently has it been possible to recover negative strand RNA viruses using recombinant reverse genetic techniques (see, e.g., U.S. Pat. No. 5,166,087, which is incorporated herein by reference in its entirety). In one embodiment of the reverse genetic technique, ribonucleoprotein complexes (RNPs) are reconstituted in vitro from RNA transcribed from plasmid DNA in the presence of influenza virus polymerase proteins (PB1, PB2 and PA) and nucleoprotein (NP) isolated from purified influenza virus (Enami et al., 1990, Proc. Natl. Acad. Sci. USA 87:3802-3805; Enami and Palese, 1991, J. Virol. 65:2711-2713; and Muster and Garcia-Sastre, Genetic manipulation of influenza viruses in Textbook of influenza (1998), ch. 9, eds. Nicholson et al.). The in vitro reconstituted RNPs are transfected into cells infected with a helper influenza virus, which provides the remaining required viral proteins and RNA segments to generate transfectant viruses. In another embodiment of the reverse genetic technique, RNPs are reconstituted intracellularly from plasmids expressing influenza virus polymerase proteins, nucleoprotein, and an influenza-like vRNA segment (Neumann et al., 1994, Virology 202:477-479; Zhang et al., 1994, Biochem. Biophys. Res. Comm. 200:95-101; and Pleschka et al., J. Virol., 1996, 70:4188-4192). The RNPs are packaged into transfectant viruses upon infection with helper influenza virus.

2.2. Influenza Virus

Virus families containing enveloped single-stranded RNA of the negative-sense genome are classified into groups having non-segmented genomes (Paramyxoviridae, Rhabdoviridae, Filoviridae and Borna Disease Virus) or those having segmented genomes (Orthomyxoviridae, Bunyaviridae and Arenaviridae). The Orthomyxoviridae family, described in detail below, and used in the examples herein, includes the viruses of influenza, types A, B and C viruses, as well as Thogoto and Dhori viruses and infectious salmon anemia virus.

The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules (seven for influenza C) of linear, negative polarity, single-stranded RNAs which encode ten polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP). Transcription and replication of the genome takes place in the nucleus and assembly occurs via budding on the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In other words, the eight viral RNA segments code for ten proteins: nine structural and one nonstructural. A summary of the genes of the influenza virus and their protein products is shown in Table 1 below.

TABLE 1

INFLUENZA VIRUS GENOME RNA SEGMENTS AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 1 | 2341 | PB2 | 759 | 30-60 | RNA transcriptase component; host cell RNA cap binding |
| 2 | 2341 | PB1 | 757 | 30-60 | RNA transcriptase component; initiation of transcription |
| 3 | 2233 | PA | 716 | 30-60 | RNA transcriptase component |
| 4 | 1778 | HA | 566 | 500 | Hemagglutinin; trimer; envelope glycoprotein; mediates attachment to cells |
| 5 | 1565 | NP | 498 | 1000 | Nucleoprotein; associated with RNA; structural component of RNA transcriptase |
| 6 | 1413 | NA | 454 | 100 | Neuraminidase; tetramer; envelope glycoprotein |
| 7 | 1027 | $M_1$ | 252 | 3000 | Matrix protein; lines inside of envelope |
|  |  | $M_2$ | 96 | ? | Structural protein in plasma membrane; spliced mRNA |
| 8 | 890 | $NS_1$ | 230 |  | Nonstructural protein; function unknown |
|  |  | NEP | 121 | ? | Nuclear export protein; spliced mRNA |

[a]Adapted from R. A. Lamb and P. W. Choppin (1983), Annual Review of Biochemistry, Volume 52, 467-506.
[b]For A/PR/8/34 strain
[c]Determined by biochemical and genetic approaches
[d]Determined by nucleotide sequence analysis and protein sequencing The influenza A virus genome contains eight segments of single-stranded RNA of negative polarity, coding for one nonstructural and nine structural proteins. The nonstructural protein NS1 is abundant in influenza virus infected cells, but has not been detected in virions. NS1 is a phosphoprotein found in the nucleus early during infection and also in the cytoplasm at later times of the viral cycle (King et al., 1975, Virology 64:378). Studies with temperature-sensitive (ts) influenza mutants carrying lesions in the NS gene suggested that the NS1 protein is a transcriptional and post-transcriptional regulator of mechanisms by which the virus is able to inhibit host cell gene expression and to stimulate viral protein synthesis. Like many other proteins that regulate post-transcriptional processes, the NS1 protein interacts with specific RNA sequences and structures. The NS1 protein has been reported to bind to different RNA species including: vRNA, poly-A, U6 snRNA, 5' untranslated region as of viral mRNAs and ds RNA (Qiu et al., 1995, RNA 1:304; Qiu et al., 1994, J. Virol. 68:425; and Hatada Fukuda 1992, J. Gen. Virol. 73:3325-9). Expression of the NS1 protein from cDNA in transfected cells has been associated with several effects: inhibition of nucleo-cytoplasmic transport of mRNA, inhibition of pre-mRNA splicing, inhibition of host mRNA polyadenylation and stimulation of translation of viral mRNA (Fortes et al., 1994, EMBO J. 13: 704; Enami et al, 1994, J. Virol. 68:1432; de la Luna et al., 1995, J. Virol. 69:2427; Lu et al., 1994, Genes Dev. 8:1817; Park et al., 1995, J. Biol. Chem. 270:28433; Nemeroff et al., 1998, Mol. Cell. 1:991; and Chen et al., 1994, EMBO J. 18:2273-83).

Influenza remains a constant worldwide threat to human health and hence there is a particular need for a ready method of generating modified influenza viruses with known mutations in any of the genomic viral RNA (vRNA) segments. Engineering influenza vRNA segments for expression of heterologous sequences is also of much interest, for example, in the development of new vaccines effective against influenza virus and a second pathogenic agent.

2.3. The Newcastle Disease Virus

The Paramyxoviridae family, described in detail below, and used in the examples herein, contain the viruses of Newcastle disease virus (NDV), parainfluenza virus, Sendai virus, simian virus 5, and mumps virus. The Newcastle disease virus is an enveloped virus containing a linear, single-strand, nonsegmented, negative sense RNA genome. The genomic RNA contains genes in the order of 3'-NP—P-M-F—HN-L, described in further detail below. The genomic RNA also contains a leader sequence at the 3' end.

The structural elements of the virion include the virus envelope which is a lipid bilayer derived from the cell plasma membrane. The glycoprotein, hemagglutinin-neuraminidase (HN) protrude from the envelope allowing the virus to contain both hemaggltitinin and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication.

The replication of all negative-strand RNA viruses, including NDV, is complicated by the absence of cellular machinery required to replicate RNA. Additionally, the negative-strand genome can not be translated directly into protein, but must first be transcribed into a positive-strand (mRNA) copy. Therefore, upon entry into a host cell, the virus can not synthesize the required RNA-dependent RNA polymerase. The L, P and NP proteins must enter the cell along with the genome on infection.

It is hypothesized that most or all of the viral proteins that transcribe NDV mRNA also carry out their replication. The mechanism that regulates the alternative uses (i.e., transcription or replication) of the same complement of proteins has not been clearly identified but appears to involve the abundance of free forms of one or more of the nucleocapsid proteins, in particular, the NP. Directly following penetration of the virus, transcription is initiated by the L protein using the negative-sense RNA in the nucleocapsid as a template. Viral RNA synthesis is regulated such that it produces monocistronic mRNAs during transcription.

Following transcription, virus genome replication is the second essential event in infection by negative-strand RNA viruses. As with other negative-strand RNA viruses, virus genome replication in Newcastle disease virus (NDV) is mediated by virus-specified proteins. The first products of replicative RNA synthesis are complementary copies (i.e., plus-polarity) of NDV genome RNA (cRNA). These plus-stranded copies (anti-genomes) differ from the plus-strand mRNA transcripts in the structure of their termini. Unlike the mRNA transcripts, the anti-genomic cRNAs are not capped and methylated at the 5' termini, and are not truncated and polyadenylated at the 3' termini. The cRNAs are coterminal with their negative strand templates and contain all the genetic information in each genomic RNA segment in the complementary form. The cRNAs serve as templates for the synthesis of NDV negative-strand viral genomes (vRNAs).

Both the NDV negative strand genomes (vRNAs) and antigenomes (cRNAs) are encapsidated by nucleocapsid proteins; the only unencapsidated RNA species are virus mRNAs. For NDV, the cytoplasm is the site of virus RNA replication, just as it is the site for transcription. Assembly of the viral components appears to take place at the host cell plasma membrane and mature virus is released by budding.

3. SUMMARY OF THE INVENTION

The present invention provides methods of generating infectious recombinant negative-strand RNA viruses intracellularly in the absence of helper virus from expression vectors comprising cDNAs encoding the viral proteins necessary to form ribonucleoprotein complexes (RNPs) and expression vectors comprising cDNA for genomic viral RNA(s) (vRNAs) or the corresponding cRNA(s). In particular, the present invention provides methods of generating infectious recombinant negative-strand RNA viruses in 293T cells in the absence of helper virus from expression vectors comprising cDNAs encoding the viral proteins necessary to form RNPs and expression vectors comprising cDNA for vRNA(s) or the corresponding cRNA(s). The infectious recombinant negative-strand RNA viruses of the invention may or may not be capable of replicating and producing progeny. The present invention encompasses methods of generating infectious recombinant negative-strand RNA viruses having segmented or non-segmented genomes.

In one embodiment, an infectious recombinant negative-strand RNA virus having a segmented or non-segmented genome is rescued in a method comprising introducing into a 293T cell expression vectors capable of expressing the genomic or antigenomic RNA segments, and a nucleoprotein, and a RNA-dependent polymerase, whereby ribonucleoprotein complexes are formed and the recombinant negative-strand RNA virus is produced in the absence of helper virus. In accordance with this embodiment, the expression of the genomic vRNA(s) or the corresponding cRNA(s) and/or the expression of the nucleoprotein and RNA-dependent RNA polymerase may be constitutive or inducible. For example, the expression of the vRNA(s) or cRNA(s) under the control of a DNA-dependent RNA polymerase promoter such as the bacteriophage T7 promoter may be induced by inducing the expression of a DNA-dependent RNA polymerase such as T7.

In another embodiment, an infectious recombinant negative-strand RNA virus having a segmented or non-segmented genome is generated in 293T cells by a method comprising: (a) introducing expression vectors capable of expressing in said cells genomic vRNA(s) or the corresponding cRNA(s); (b) introducing expression vectors capable of expressing in said cells a nucleoprotein and an RNA-dependent RNA polymerase; and (c) culturing said cells such that RNPs are formed and the recombinant negative-strand RNA virus is produced in the absence of helper virus. In accordance with the present invention, the expression vector may be engineered to express the genomic RNA segments, the nucleoprotein and the RNA-dependent polymerase, or any combination thereof. In another embodiment, each component may be provided to the cell in individual expression vectors.

In another yet another embodiment, infectious recombinant negative-strand RNA viruses are rescued in 293T cells by a method comprising introducing expression vectors capable of expressing in said cells genomic RNAs or antigenomic RNAs in cells which express a nucleoprotein and an RNA dependent polymerase and culturing said cells such that RNP's are formed and the virus is produced in the absence of helper virus.

The present invention also provides methods of generating an infectious recombinant negative-strand RNA viruses having greater than 3 genomic vRNA segments in host cells, said methods comprising: (a) expressing genomic vRNA segments or the corresponding cRNAs from a first set of expression vectors in said cells; and (b) expressing a nucleoprotein and an RNA-dependent RNA polymerase from a second set of recombinant expression vectors in said cells, whereby ribonucleoprotein complexes are formed and the infectious recombinant negative-strand RNA viruses are produced in the absence of helper virus. Preferably, the infectious recombinant negative-strand RNA virus generated is a member of the Orthomyxoviridae family and most preferably the infectious recombinant negative-strand RNA virus generated is an influenza virus.

In one embodiment, an infectious recombinant negative-strand RNA virus having greater than 3 genomic vRNA segments is generated in host cells by a method comprising: (a) introducing a first set of expression vectors capable of expressing in said cells genomic vRNA segments or the corresponding cRNAs; (b) introducing a second set of expression vectors capable of expressing in said cells a nucleoprotein and an RNA-dependent RNA polymerase; and (c) culturing said cells such that RNPs are formed and the infectious recombinant negative-strand RNA virus is produced in the absence of helper virus.

In another embodiment, an infectious recombinant negative-strand RNA virus having greater than 3 genomic vRNA segments is generated in a host cell line expressing a nucleoprotein and an RNA-dependent RNA polymerase by a method comprising: (a) introducing expression vectors capable of expressing in said cell line genomic vRNA segments or the corresponding cRNAs; and (b) culturing said cells such that RNPs are formed and the infectious recombinant negative-strand RNA virus is produced in the absence helper virus. In another embodiment, an infectious recombinant negative-strand RNA virus having greater than 3 genomic vRNA segments is generated in a mammalian cell line expressing genomic vRNA segments or the corresponding cRNAs by a method comprising: (a) introducing expression vectors capable of expressing a nucleoprotein and an RNA-dependent RNA polymerase; and (b) culturing said cells such that RNPs are formed and the infectious recombinant negative-strand RNA virus is produced in the absence of helper virus.

The present invention is based, in part, on Applicants' identification of the correct nucleotide sequence of the 5' and 3' temini of the negative-sense genomes RNA of NDV. The nucleotide sequence of the 3' termini of the NDV negative-sense genome RNA of the present invention differs significantly from the NDV 3' termini sequence previously disclosed by Collins et al. in Fundamental Virology 3rd Ed. 1996 by Lippincott-Raven Publishers as shown in FIG. 6. The identification of the correct nucleotide sequence of the NDV 3' termini allows for the first time the engineering of recombinant NDV RNA templates, the expression of the recombinant RNA templates and the rescue of recombinant NDV particles. Accordingly, the present invention provides methods of generating an infectious, replicating recombinant Newcastle disease virus (NDV) in mammalian cells, said methods comprising: (a) expressing a genomic vRNA or the corresponding cRNA from an expression vector in said cells; and (b) expressing a nucleoprotein and an RNA-dependent RNA polymerase from a set of expression vectors in said cells, whereby ribonucleoprotein complexes are formed and the recombinant NDV is produced in the absence of helper virus.

In one embodiment, an infectious recombinant NDV is generated in host cells by a method comprising: (a) introducing an expression vector capable of expressing in said cells genomic vRNA or the corresponding cRNA; (b) introducing a set of expression vectors capable of expressing in said cells a nucleoprotein and an RNA-dependent RNA polymerase; and (c) culturing said cells such that RNPs are formed and recombinant NDV is produced in the absence of helper virus.

In another embodiment, an infectious recombinant NDV is generated in a host cell line expressing a nucleoprotein and an RNA-dependent RNA polymerase by a method comprising: (a) introducing expression vectors capable of expressing in said cell line a genomic vRNA or the corresponding cRNA; and (b) culturing said cell line such that RNPs are formed and recombinant NDV is produced in the absence helper virus. In another embodiment, an infectious recombinant NDV is generated in a host cell line expressing a genomic vRNA segment or the corresponding cRNA by a method comprising: (a) introducing expression vectors capable of expressing in said cell line a nucleoprotein and an RNA-dependent RNA polymerase; and (b) culturing said cell line such that RNPs are formed and recombinant NDV is produced in the absence of helper virus.

The ability to reconstitute negative-strand RNA viruses intracellularly allows the design of novel recombinant viruses (i.e., chimeric viruses) which express heterologous nucleic acid sequences or which express mutant viral genes. The heterologous sequences may encode, for example, epitopes or antigens of pathogens or tumors. The ability to reconstitute negative-strand RNA viruses intracellularly also allows the design of novel recombinant viruses (i.e., chimeric viruses) which express genes from different strains of viruses. Thus, the present invention provides methods of generating chimeric viruses which express heterologous nucleic acid sequences, mutant viral genes, or viral genes from different strains of virus intracellularly from expression vectors.

The present invention provides for the use of the recombinant negative-strand RNA viruses or chimeric viruses of the invention to formulate vaccines against a broad range of viruses and/or antigens including tumor antigens. The recombinant negative-strand RNA viruses or chimeric viruses of the present invention may be used to modulate a subject's immune system by stimulating a humoral immune response, a cellular immune response or by stimulating tolerance to an antigen. When delivering, tumor antigens, the invention may be used to treat subjects having a disease amenable to immunity mediated rejection, such as non-solid tumors or solid tumors of small size. It is also contemplated that delivery of tumor antigens by the recombinant negative-strand RNA viruses or chimeric viruses described herein will be useful for treatment subsequent to removal of large solid tumors. The recombinant negative-strand RNA viruses or chimeric viruses of the invention may also be used to treat subjects who are suspected of having cancer.

The present invention also provides for the use of the recombinant negative-strand RNA viruses or chimeric viruses of the invention in pharmaceutical compositions for the administration of peptides or polypeptides to a subject.

3.1. Definitions

As used herein, the following terms will have the meanings indicated:

cRNA=anti-genomic RNA
HIV=human immunodefiency virus
L=large protein
M=matrix protein (lines inside of envelope)
MDCK=Madin Darby canine kidney cells
MDBK=Madin Darby bovine kidney cells
MLP=adenovirus type 2 major late promoter linked to a synthetic sequence comprising the spliced tripartite leader sequence of human adenovirus type 2
moi=multiplicity of infection
NA=neuraminidase (envelope glycoprotein)
NDV=Newcastle disease Virus
NP=nucleoprotein (associated with RNA and required for polymerase activity)
NS=nonstructural protein (function unknown)
nt=nucleotide
PA, PB1, PB2=RNA-directed RNA polym erase components
pA=polyadenylation sequence from SV40
POLI=truncated human RNA polymerase I promoter
R=genomic hepatitis virus ribozyme
RNP=ribonucleoprotein (RNA, PB2, PB1, PA and NP)
rRNP=recombinant RNP
vRNA=virus RNA
viral polymerase complex=PA, PB 1, PB2 and NP
WSN=influenza A/WSN/33 virus
WSN-HK virus=reassortment virus containing seven genes from WSN virus and the NA gene from influenza A/HK/8/68 virus The term "expression vectors" as used herein refers to plasmids, viral vectors, recombinant nucleic acids and cDNA. Preferably, the term "expression vectors" refers to plasmids.

The term "helper virus" as used herein refers to a virus homologous to the virus being rescued. The helper virus generally supplies one or more of the viral proteins which are required for the production of infectious recombinant negative-strand RNA vinises.

4. DESCRIPTION OF THE FIGURES

FIG. 1. Schematic representation of a method of generating recombinant influenza virus. Eight transcription plasmids encoding the vRNA segments of an influenza A virus and four protein expression plasmids encoding influenza A virus nucleoprotein and RNA-dependent RNA polymerase subunits are cotransfected into cultured Vero cells (African green monkey kidney cells). Then, MDBK (Madin-Darby bovine kidney) cells are employed for plaque assay and amplification of rescued viral particles.

Figure 2:
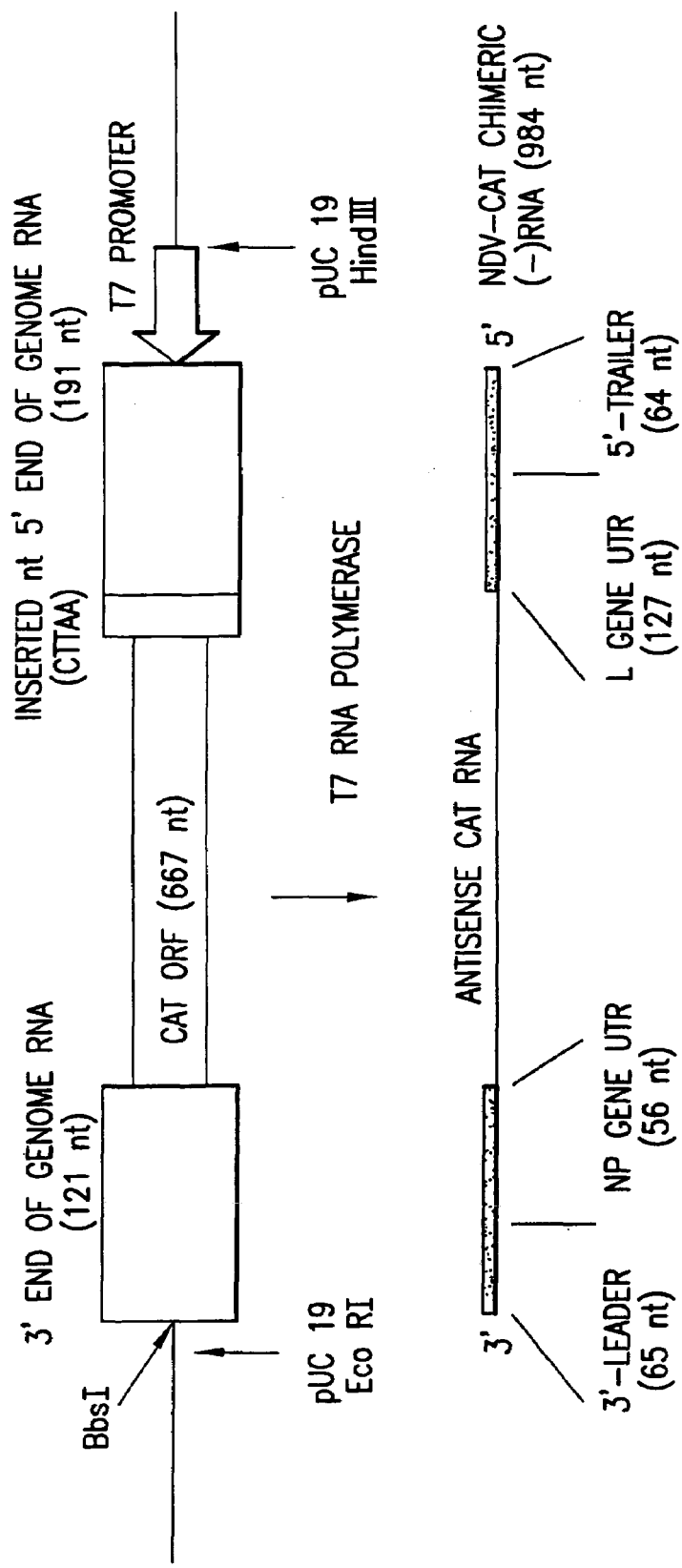

FIG. 2. Schematic representation of the NDV minigenome. Top illustration depicts the PNDVCAT plasmid including the T7 promoter; the 5' terminal sequence (5' end of genomic RNA, 191nt); the inserted nucleotides (CT-TAA); 667 nt of CAT ORF; the 3' terminal sequence (3' end of genomic RNA, 121 nt) the BbS1 and nuclease sites. Lower illustration depicts the chimeric NDV-CAT RNA resulting from in vitro transcription.

Figure 3A:
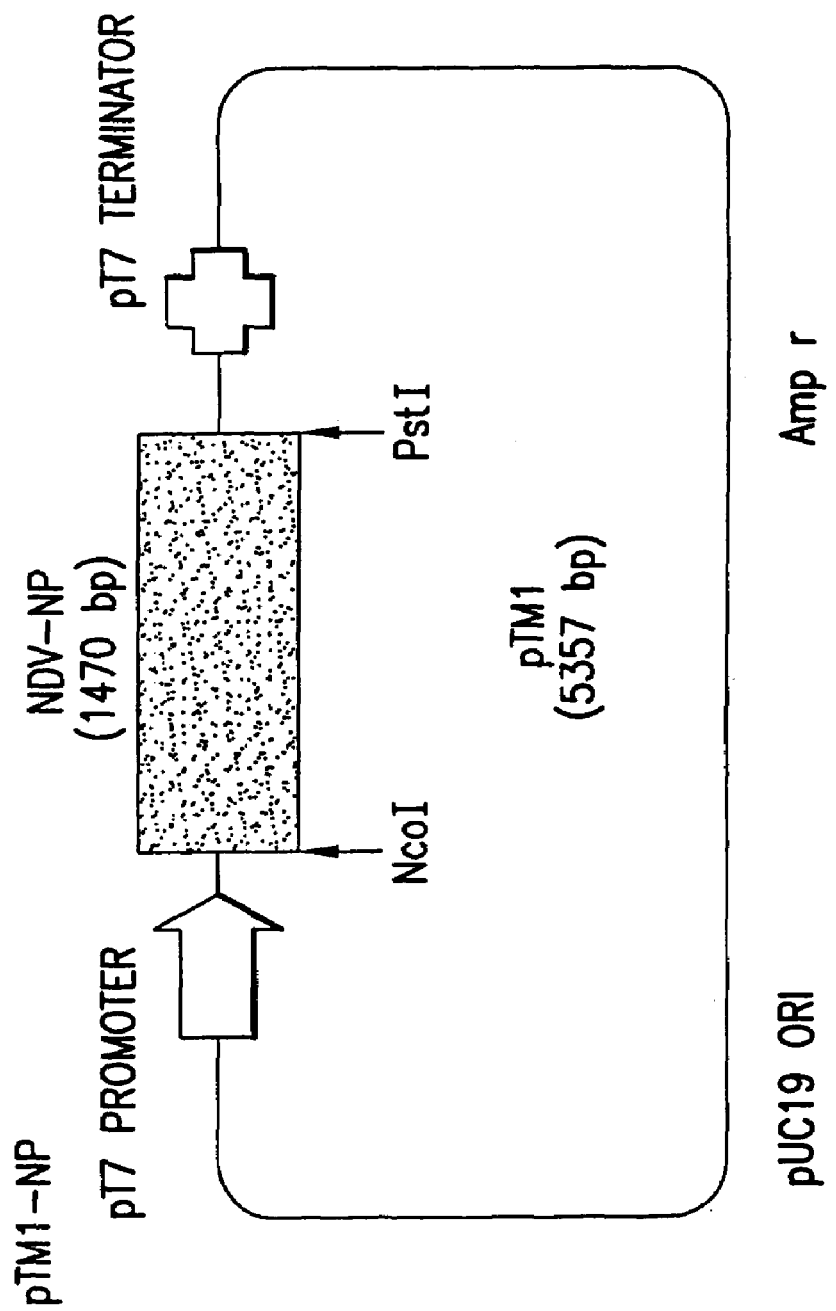
Figure 3B:
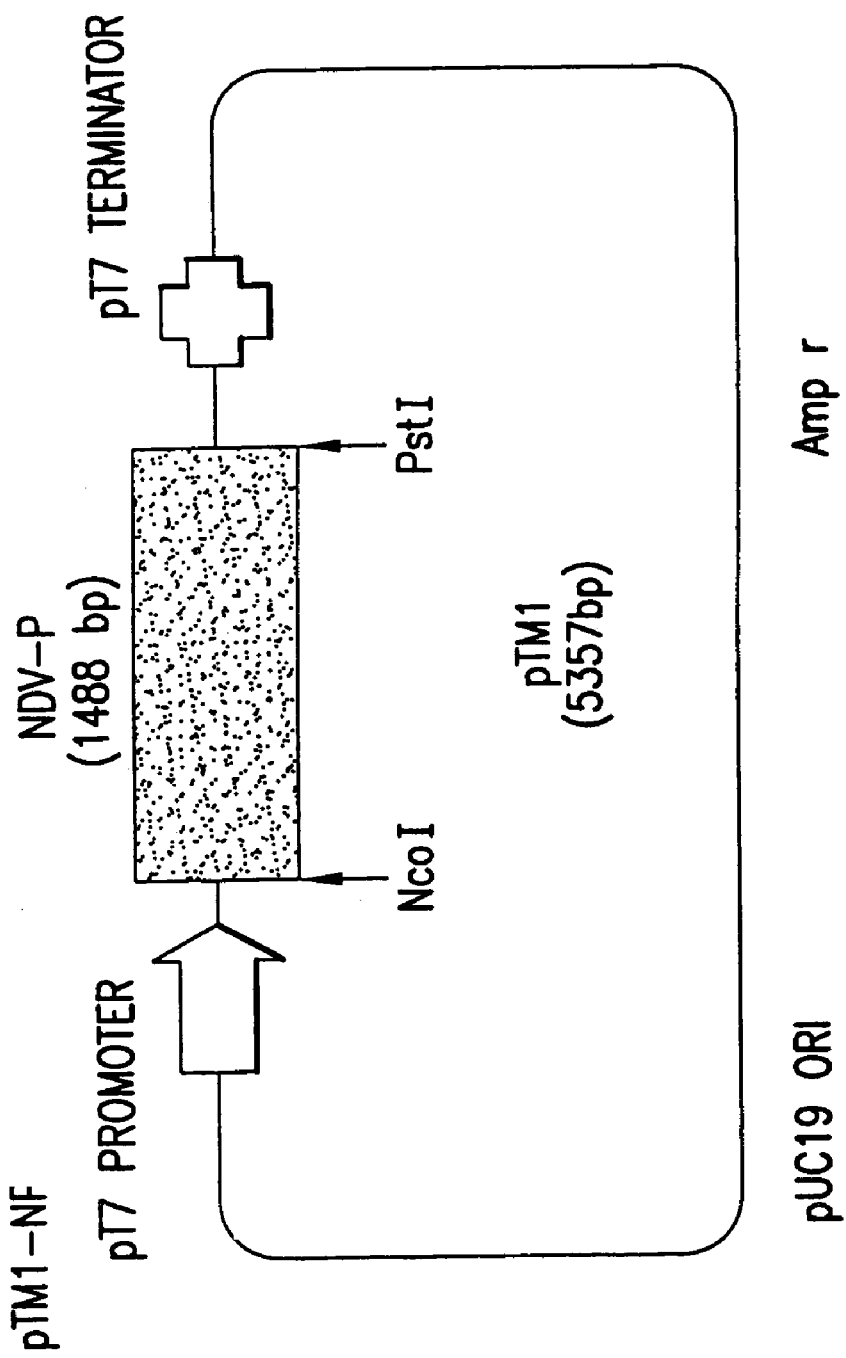
Figure 3C:
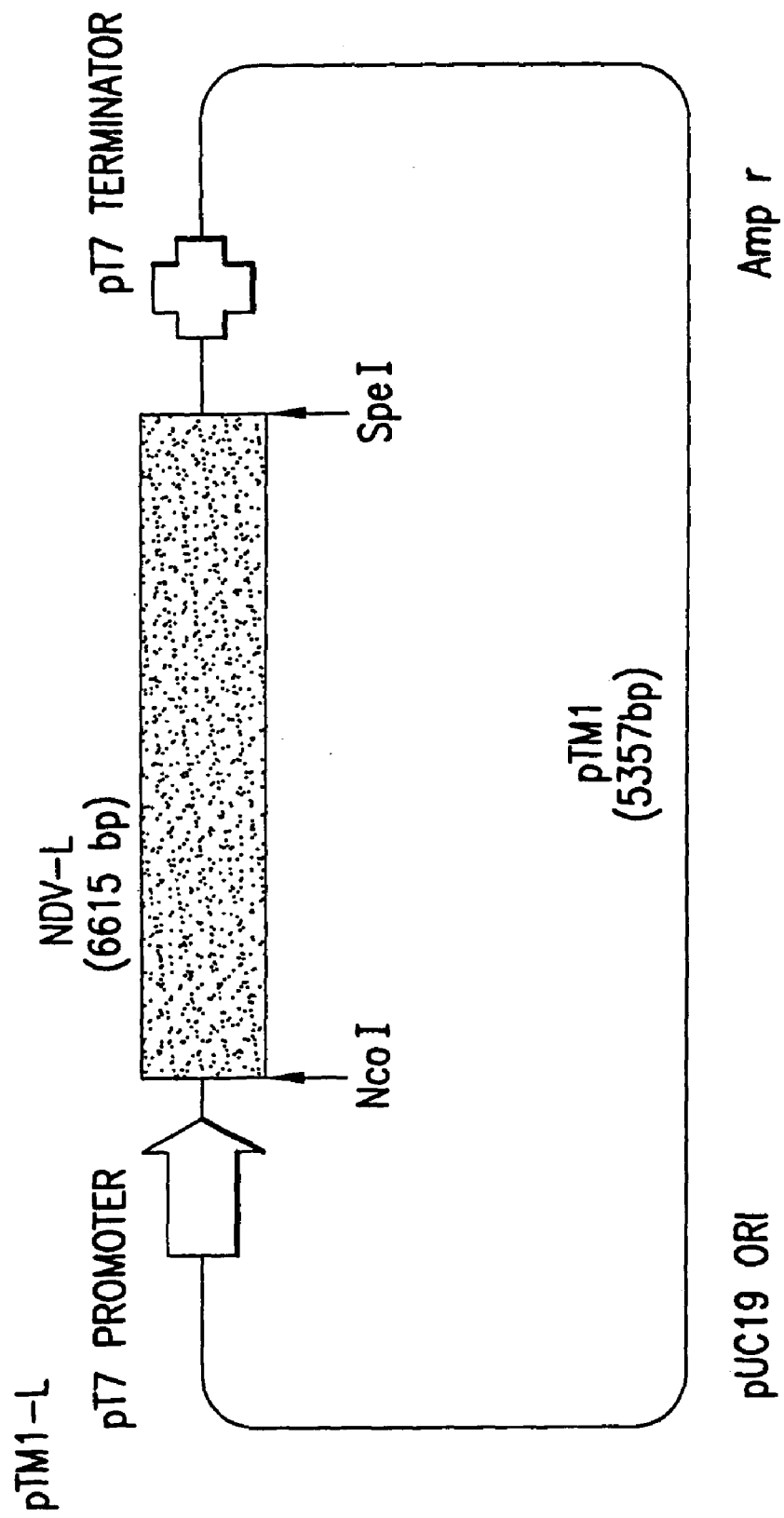

FIGS. 3A-3C. Schematic representation of the PTMI expression vectors.
PTM 1-NP encodes the NDV NP protein.
PTM 1-P encodes the NDV P protein.
PTM1-L encodes the NDV L protein.

FIG. 4. RNA sequence of NDV 5' and 3' non-coding terminal regions (plus-sense). Sequences 5' to the CAT gene represent 121nt (SEQ ID NO: 1) of the 5' non-coding terminal region of NDV plus sense genome comprising 65 nt of the leader sequence (in bold) followed by 56 nt of the NP gene UTR. Sequences 3' to the CAT gene represent inserted nucleotides cuuaa (in lower case) and 191 nt (SEQ ID NO: 2) of the non-coding terminal region of NDV plus sense genome comprising 127nt of the UTR of the L gene followed by 64nt of the trailer region (in bold).

Figure 5A:
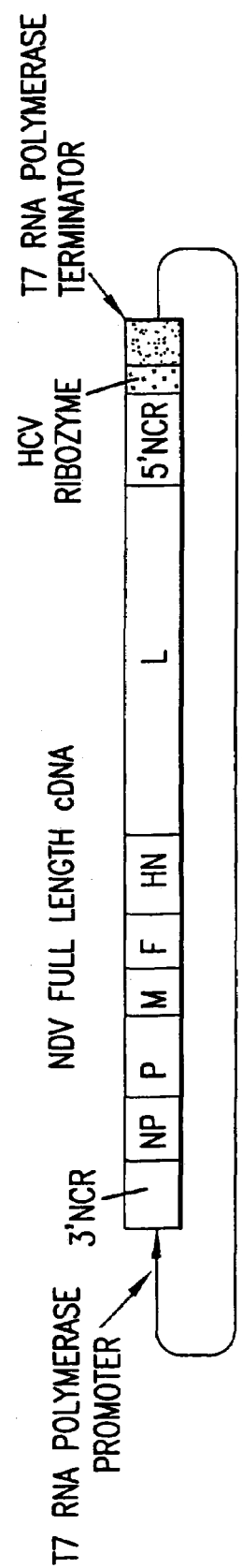
Figure 5B:
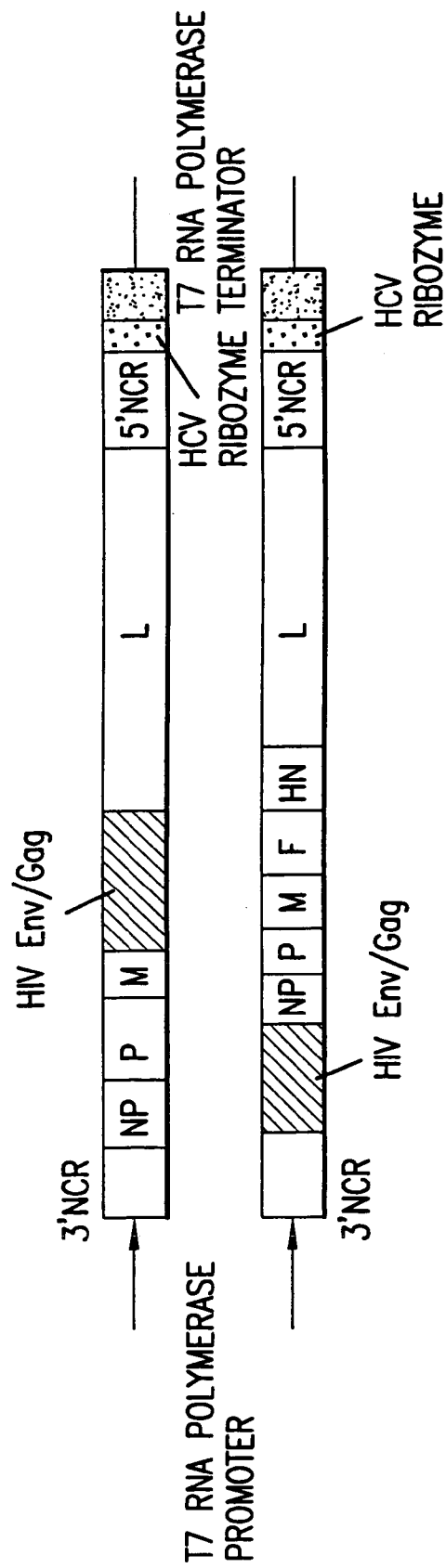

FIGS. 5A-5B. Schematic representation of a structure of recombinant NDV clones. FIG. 4B, representation of infectious NDV expressing HIV Env and Gag. Top panel, HIV Env and Gag are between the M and L genes. Lower panel, HIV Env and Gag are 3' to the NP gene.

FIG. 6. Schematic representation of the 3' termini of NDV (SEQ ID NO: 3) as aligned with sequence (SEQ ID NO: 4) of Collins et al. Parainfluenza viruses, in Field's Virology, 3rd ed. B. N. Fields, D. M. Knipe, p.m. Howley et al, eds., Lippincott-Raven Publishing, Philidalplia, 1996.

5. DETAILED DESCRIPTION OF THE INVENTION

The present invention provides methods of generating infectious negative-strand RNA viruses intracellularly from recombinant nucleic acid molecules. In particular, the present invention provides methods of generating an infectious negative-strand RNA virus in 293T cells, said methods comprising providing expression vectors capable of expressing genomic or antigenomic viral RNA segments, and nucleoproteins, and RNA dependent RNA polymerase, whereby RNPs are formed in said cells and infectious recombinant negative-strand RNA is produced in the absence of helper virus. The present invention encompasses methods of infectious recombinant negative-strand RNA virus having a segmented or non-segmented genome.

The present invention provides methods of generating infectious, replicating recombinant negative-strand RNA virus in the absence of helper virus by transiently transfecting 293T cells with expression vectors providing the genomic vRNA(s) or the corresponding cRNA(s) and the required viral proteins. In one embodiment, an infectious, replicating negative-strand RNA virus is generated in 293T cells by a method comprising: (a) introducing expression vectors which direct the expression of each required genomic vRNA segment or the corresponding cRNA into said cells; (b) introducing expression vectors which express a nucleoprotein and RNA-dependent RNA polymerase subunits or one or more additional viral proteins in said cells; and (c) culturing said cells such that RNPs are formed and the infectious, replicating recombinant negative-strand RNA virus is produced in the absence of helper virus. In accordance with these embodiments, each set of expression vectors may each comprise one or more vectors and each set of expression vectors may be introduced by transfection methods described herein or known to those of skill in the art.

The present invention also provides methods of generating infectious, replicating recombinant negative-strand RNA virus in the absence of helper virus by transfecting 293T cell lines expressing one or more genomic vRNAs or the corresponding cRNAs with expression vectors directing the expression of the required viral proteins. In a specific embodiment, an infectious, replicating recombinant negative-strand RNA virus is generated in a 293T cell line expressing genomic vRNA(s) or the corresponding cRNA(s) by a method comprising: (a) introducing expression vectors which express in said cells a nucleoprotein and RNA-dependent RNA polymerase subunits; and (b) culturing said cells such that RNPs are formed and the infectious, replicating virus is produced in the absence of helper virus.

The present invention also provides methods of generating infectious, replicating recombinant negative-strand RNA virus in the absence of helper virus in a 293T cell line that expresses one or more viral proteins required to form RNPs (i.e., nucleoprotein and RNA-dependent RNA polymerase subunits), said methods comprising: (a) introducing one or more expression vectors directing the expression of genomic vRNA(s) or the corresponding cRNA(s) in said cell line; (b) introducing one or more expression vectors that direct the expression of any viral proteins required to form RNPs which are not expressed by the 293T cell line; and (c) culturing said cell lines such that RNPs are formed and the infectious recombinant virus is produced. In accordance with this embodiment, each set of expression vectors may each comprise one or more vectors. For example, in the generation of an infectious, replicating negative-strand RNA virus with a nonsegmented genome, the first set of expression vectors would comprise one expression vector.

In accordance with the present invention, the 293 T cells, or any other host cell used in the methods of the invention, may be modified in many ways in order to facilitate rescue of a recombinant negative strand RNA virus in the absence of helper virus. In particular, the host cell may be modified or engineered to express viral proteins required for replication or packaging, either constitutively or inducibly. In either event, expression of the viral proteins is regulated by either a constitutive or inducible promoter as described herein or known to those of skill in the art. In such an embodiment, the host cell may be engineered to express viral proteins required to form RNPs or viral structured proteins. In another embodiment, the host cell may be modified to constitutively or inducibly expresses RNA-dependent RNA polymerases, or subunits thereof.

The present invention also provides methods of generating infectious, non-replicating or attenuated negative-strand RNA virus in 293T cells in the absence of helper virus, wherein method comprises introducing expression vectors which do not encode all of the genomic viral sequences required to form viral particles; or introducing expression vectors which provide the genomic vRNA(s) or corresponding cRNA(s) which contain a mutation, deletion or insertion which result in a recombinant virus with an attenuated phenotype. Further, the expression vectors may be introduced by transfection methods described herein or known to those of skill in the art.

The present invention also provides methods of generating infectious negative strand RNA virus in 293T cells infected by a helper virus, said methods comprising: (a) introducing expression vectors directing the expression of one or more vRNAs or the corresponding cRNAs in said cells; (b) introducing expression vectors directing the expression of one or more viral proteins in said cells; and (c) culturing the cells such that the RNPs are formed and the infectious, replicating negative-strand RNA virus is produced. In one embodiment, the helper virus provides viral proteins required to form the RNPs. In a preferred embodiment, the helper virus provides a DNA-dependent RNA polymerase such as, for example, bacteriophage T7, T3 or the SP6 polymerase. Preferably, the helper virus is not a negative-strand RNA virus and more preferably the helper virus is a DNA virus such as vaccinia.

The present invention also provides methods of generating infectious negative strand RNA virus in a 293T cell line infected by helper virus by introducing one or more expression vectors into said cell line. Accordingly, the 293T cell lines are transfected with expression vectors that direct the expression of vRNA(s) or the corresponding cRNA(s) and expression vectors that direct the expression of the viral proteins required for the formation of RNPs which are not provided by the helper virus.

The present invention also provides methods of generating an infectious recombinant negative-strand RNA viruses having greater than 3 genomic vRNA segments in mammalian cells, said methods comprising: (a) expressing genomic vRNA segments or the corresponding cRNAs from a first set of expression vectors in said cells; and (b) expressing a nucleoprotein and an RNA-dependent RNA polymerase from a second set of recombinant expression vectors in said cells, whereby ribonucleoprotein complexes are formed and the infectious recombinant negative-strand RNA viruses are produced in the absence of helper virus. Preferably, the infectious recombinant negative-strand RNA virus is a member of the Orthomyxoviridae family and most preferably the infectious-recombinant negative-strand RNA virus is an influenza virus.

The present invention encompasses the generation of infectious recombinant negative-strand RNA viruses having greater than 3 genomic segments which are capable of replicating and producing progeny. The invention also encompasses the infectious recombinant negative-strand RNA viruses having greater than 3 genomic segments which are not capable of replicating and producing progeny.

In one embodiment, an infectious recombinant negative-strand RNA virus having greater than 3 genomic vRNA segments is generated in mammalian cells by a method comprising: (a) introducing a first set of expression vectors capable of expressing in said cells genomic vRNA segments or the corresponding cRNAs; (b) introducing a second set of expression vectors capable of expressing in said cells a nucleoprotein and RNA-dependent RNA polymerase; and (c) culturing said cells such that RNPs are formed and the infectious recombinant negative-strand RNA virus is produced in the absence of helper virus.

In another embodiment, an infectious recombinant negative-strand RNA virus having greater than 3 genomic vRNA segments is generated in a mammalian cell line expressing a nucleoprotein and an RNA-dependent RNA polymerase by a method comprising: (a) introducing expression vectors capable of expressing genomic vRNA segments or the corresponding cRNAs; and (b) culturing said cells such that RNPs are formed and the infectious recombinant negative-strand RNA virus is produced in the absence helper virus. In another embodiment, an infectious recombinant negative-strand RNA virus having greater than 3 genomic vRNA segments is generated in a mammalian cell line expressing genomic vRNA segments or the corresponding cRNAs by a method comprising: (a) introducing expression vectors capable of expressing a nucleoprotein and an RNA-dependent RNA polymerase; and (b) culturing said cells such that RNPs are formed and the infectious recombinant negative-strand RNA virus is produced in the absence of helper virus.

The present invention also provides methods of generating infectious recombinant negative-strand RNA viruses having greater than 3 vRNA segments in the presence of helper virus by introducing into host cells expression vectors. The expression vectors introduced into the host cells comprise vectors directing the expression of greater than 3 vRNA segments or the corresponding cRNAs. Further, the expression vectors introduced into the host cells may comprise cDNA encoding one or more viral proteins, particularly one or more viral proteins required to form the RNPs.

The present invention provides methods of generating an infectious, replicating recombinant Newcastle disease virus (NDV) in mammalian cells, said methods comprising: (a) expressing genomic vRNA or the corresponding cRNA from an expression vector in said cells; and (b) expressing a nucleoprotein and an RNA-dependent RNA polymerase from a set of expression vectors in said cells, whereby ribonucleoprotein complexes are formed and the recombinant NDV is produced in the absence of helper virus. The present invention provides methods of generating an infectious, non-replicating recombinant Newcastle disease virus (NDV) in mammalian cells, said methods comprising: (a) expressing a vRNA or the corresponding cRNA from an expression vector in said cells, wherein said vRNA or the corresponding cRNA do not encode of the genomic viral proteins necessary for replicating; and (b) expressing a nucleoprotein and an RNA-dependent RNA polymerase from a set of expression vectors in said cells, whereby ribonucleoprotein complexes are formed and the non-replicating recombinant NDV is produced in the absence of helper virus.

In one embodiment, an infectious recombinant NDV is generated in mammalian cells by a method comprising: (a) introducing an expression vectors capable of expressing in said cells a genomic vRNA or the corresponding cRNA; (b) introducing a set of expression vectors capable of expressing in said cells a nucleoprotein and RNA-dependent RNA polymerase; and (c) culturing said cells such that RNPs are formed and recombinant NDV is produced in the absence of helper virus.

In another embodiment, an infectious recombinant NDV is generated in a host cell line expressing a nucleoprotein and an RNA-dependent RNA polymerase by a method comprising: (a) introducing expression vectors capable of expressing in said cell line a genomic vRNA segment or the corresponding cRNA; and (b) culturing said cell line such that RNPs are formed and recombinant NDV is produced in the absence helper virus. In another embodiment, an infectious recombinant NDV is generated in a host cell line expressing a genomic vRNA or the corresponding cRNA by a method comprising: (a) introducing expression vectors capable of expressing in said cell line a nucleoprotein and an RNA-dependent RNA polymerase; and (b) culturing said cell line such that RNPs are formed and recombinant NDV is produced in the absence of helper virus.

The present invention also encompasses methods of generating NDV in the presence of helper virus by introducing expression vectors. The expression vectors directing the expression of genomic vRNA or cRNA and/or one or more viral proteins.

The ability to reconstitute negative-strand RNA viruses intracellularly in mammalian cells allows for the design of recombinant viruses (i.e., chimeric viruses) which express heterologous nucleic acid sequences or mutant viral genes. The heterologous sequences may encode, for example, epitopes or antigens of pathogens or tumors. The ability to reconstitute negative-strand RNA viruses intracellularly also allows the design of novel recombinant viruses (i.e., chimeric viruses) which express genes from different strains of viruses. Thus, the present invention provides methods of generating chimeric viruses which express heterologous nucleic acid sequences, mutant viral genes, or viral genes from different strains of virus intracellularly from expression vectors in the absence or presence of helper virus.

The present invention encompasses the cells and cell lines produced in the process of generating infectious negative-strand RNA viruses.

The infectiousness of a recombinant or chimeric negative-strand RNA virus of the present invention will vary depending upon the strain of virus from which the nucleic acid sequences encoding structural proteins such as influenza virus HA or NA are derived. Additionally, the infectiousness of a recombinant or chimeric negative-strand RNA virus of the invention will vary depending upon whether or not mutations have been introduced into the nucleic acid sequences encoding structural proteins. For example, a recombinant influenza virus of the invention with a mutation in HA may not be as infectious as another recombinant influenza virus expressing identical viral proteins without a mutation in HA.

The infectious recombinant or chimeric viruses of the present invention may or may not be capable of replicating and producing progeny. In a specific embodiment, an infectious recombinant negative-strand RNA virus of the invention is capable of replicating and producing progeny. The replication of an infectious recombinant or chimeric negative-strand RNA virus of the invention will vary depending upon the strain of virus from which the genomic vRNA(s) or the corresponding cRNA(s) were derived. Further, the replication of an infectious recombinant or chimeric negative-strand RNA virus of the invention will vary depending upon whether or not mutations have been introduced into the genomic vRNA(s) or the corresponding cRNA(s). For example, an infectious recombinant influenza virus expressing a truncated NS1 protein may replicate better than an infectious recombinant influenza virus expressing identical viral proteins except that it expresses a full-length NS1 protein.

The present invention provides for the use of the recombinant negative-strand RNA viruses or chimeric viruses of the invention to formulate vaccines against a broad range of viruses and/or antigens including tumor antigens. The recombinant negative-strand RNA viruses or chimeric viruses of the present invention may be used to modulate a subject's immune system by stimulating a humoral immune response, a cellular immune response or by stimulating tolerance to an antigen. When delivering, tumor antigens, the invention may be used to treat subjects having a disease amenable to immunity mediated rejection, such as non-solid tumors or solid tumors of small size. It is also contemplated that delivery of tumor antigens by the recombinant negative-strand RNA viruses or chimeric viruses described herein will be useful for treatment subsequent to removal of large solid tumors. The recombinant negative-strand RNA viruses or chimeric viruses of the invention may also be used to treat subjects who are suspected of having cancer.

The present invention also provides for the use of the recombinant negative-strand RNA viruses or chimeric viruses of the invention in pharmaceutical compositions for the administration of one or more peptides or polypeptides of interest.

5.1. Expression Vectors for vRNA

Expression vectors comprising cDNA for viral RNA(s) or corresponding cRNA(s) will preferably be under the control of a DNA-dependent RNA polymerase promoter sequence. Examples of DNA-dependent RNA polymerase promoters include but are not limited to, bacterial promoters, viral promoters such as T7, T3 or SP3, and cellular promoters such as a mammalian RNA polymerase I promoter. Preferably, the cDNA for the viral RNA(s) or corresponding cRNA(s) is derived from a mammalian RNA polymerase I (RNA Pol I) promoter. Particularly preferred for this purpose is the truncated human RNA Pol I promoter consisting of nucleotides −250 to −1 of the corresponding native promoter or a functional derivative thereof (Jones et al., 1988, Proc. Natl. Acad. Sci. USA 85:669-673). In yet another embodiment, the vRNA(s) or corresponding cRNA(s) may be under the control of a mammalian RNA polymerase II promoter or RNA polymerase III promoter (see, e.g. Legin in Genes, Oxford University Press, New York (1977), pp. 819-22). To ensure the correct 3' end of each expressed vRNA or cRNA, each vRNA or cRNA expression vector will incorporate a ribozyme sequence or appropriate terminator sequence downstream of the RNA coding sequence. This may be, for example, the hepatitis delta virus genomic ribozyme sequence or a functional derivative thereof, or the murine rDNA terminator sequence (Genbank Accession Number M12074). Alternatively, for example, a PolI terminator may be employed (Neumann et al., 1994, Virology 202:477-479). The RNA expression vectors may be constructed in the same manner as the vRNA expression vectors described in Pleschka et al., 1996, J. Virol. 70:4188-4192.

In a specific embodiment of the present invention, vRNA or cRNA expression vectors for the production of infectious recombinant NDV comprise the nucleotide sequence of the 3' termini of the NDV negative-sense genome RNA first identified by the Applicants'. This 3' termini of the NDV negative-sense genome RNA differs significantly from the NDV 3' termini sequence previously disclosed by Collins et al. in Fundamental Virology 3rd Ed. 1996 by Lippincott-Raven Publishers as shown in FIG. 6. The identification of the correct nucleotide sequence of the NDV 3' termini allows for the first time the engineering of recombinant NDV RNA templates, the expression of the recombinant RNA templates and the rescue of recombinant NDV particles.

A DNA-dependent RNA polymerase which recognizes the promoter sequence in the vRNA or corresponding cRNA expression vectors is used to produce the vRNA or corresponding cRNA from the nucleic acid sequences. Examples of DNA-dependent RNA polymerases include, but are not limited to, viral DNA-dependent RNA polymerase such as T7, T3 or the SP6 polymerase, bacterial DNA-dependent RNA polymerase, and cellular DNA-dependent RNA such as mammalian RNA polymerase I. In one embodiment, the expression vectors comprising the cDNA directing the expression of vRNA(s) or corresponding cRNA(s) are introduced into a host cell that does not express the DNA-dependent RNA polymerase which recognizes the DNA-dependent RNA polymerase promoter and one or more vectors expressing the DNA-dependent RNA polymerase subunits are introduced into said host cell. In accordance with this embodiment, the vectors expressing the DNA-dependent RNA polymerase subunits may be regulated by an inducible promoter. The expression of the DNA-dependent RNA polymerase then regulates the expression of the vRNA(s) or corresponding cRNAs.

The present invention provides expression vectors directing the expressing of genomic vRNA(s) or corresponding cRNA(s) which have one or more mutations. These mutations may result in the attenuation of the virus. For example, the vRNA segments may be the vRNA segments of an influenza A virus having an attenuated base pair substitution in a pan-handle duplex promoter region, in particular, for example, the known attenuating base pair substitution of A for C and U for G at position 11-12' in the duplex region of the NA-specific vRNA (Fodor et al., 1998, J. Virol. 6923-6290). By using the methods of the invention to produce recombinant negative-strand RNA virus, new attenuating mutations may be identified.

Sequences heterologous to a viral genome may be engineered into expression vectors directing the expression of vRNA(s) or corresponding cRNA(s) and introduced into host cells along with expression vectors directing the expression of viral proteins to generate novel infectious recombinant negative-strand RNA viruses or chimeric viruses. Heterologous sequences which may be engineered into these viruses include antisense nucleic acids and nucleic acid such as a ribozyme. Alternatively, heterologous sequences which express a peptide or polypeptide may be engineered into these viruses. Heterologous sequences encoding the following peptides or polypeptides may be engineered into these viruses include: 1) antigens that are characteristic of a pathogen; 2) antigens that are characteristic of autoimmune disease; 3) antigens that are characteristic of an allergen; and 4) antigens that are characteristic of a tumor. For example, heterologous gene sequences that can be engineered into the chimeric viruses of the invention include, but are not limited to, epitopes of human immunodeficiency virus (HIV) such as gp160; hepatitis B virus surface antigen (HBsAg); the glycoproteins of herpes virus (e.g., gD, gE); VP1 of poliovirus; and antigenic determinants of nonviral pathogens such as bacteria and parasites to name but a few.

Antigens that are characteristic of autoimmune disease typically will be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discoid lupus erythromatosus.

Antigens that are allergens are generally proteins or glycoproteins, including antigens derived from pollens, dust, molds, spores, dander, insects and foods.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within an negative-strand RNA virus gene coding sequence such that a chimeric gene product is expressed which contains the heterologous peptide sequence within the viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

One approach for constructing these hybrid molecules is to insert the heterologous coding sequence into a DNA complement of a negative-strand RNA virus gene so that the heterologous sequence is flanked by the viral sequences required for viral polymerase activity; i.e., the viral polymerase binding site/promoter, hereinafter referred to as the viral polymerase binding site, and a polyadenylation site. In an alternative approach, oligonucleotides encoding the viral polymerase binding site, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82:488). Variations in polymerase chain reaction (PCR) technology, described, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophase T3, T7 or SP6) and the hybrid sequence containing the heterologous gene and the polymerase binding site. RNA templates could then be transcribed directly from this recombinant DNA. In yet another embodiment, the recombinant vRNAs or corresponding cRNAs may be prepared by ligating RNAs specifying the negative polarity of the heterologous gene and the viral polymerase binding site using an RNA ligase.

Bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with Newcastle disease virus packaging limitations. Thus, it is preferable that the IRES chosen for such a bicistronic approach be no more than 500 nucleotides in length, with less than 250 nucleotides being preferred. Further, it is preferable that the IRES utilized not share sequence or structural homology with picornaviral elements. Preferred IRES elements include, but are not limited to the mammalian BiP IRES and the hepatitis C virus IRES.

Alternatively, a foreign protein may be expressed from an internal transcriptional unit in which the transcriptional unit has an initiation site and polyadenylation site. In another embodiment, the foreign gene is inserted into a negative-strand RNA virus gene such that the resulting expressed protein is a fusion protein.

5.2. Expression Vectors Encoding Viral Proteins

Expression vectors used to express viral proteins, in particular viral proteins for RNP complex formation, will preferably express viral proteins homologous to the desired virus. The expression of viral proteins by these expression vectors may be regulated by any regulatory sequence known to those of skill in the art. The regulatory sequence may be a constitutive promoter, an inducible promoter or a tissue-specific promoter. In a specific embodiment, the regulatory sequence comprises the adenovirus 2 major late promoter linked to the spliced tripartite leader sequence of human adenovirus 2, as described by Berg et al., BioTechniques 14:972-978.

Promoters which may be used to control the expression of viral proteins in protein expression vectors include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster.et al., 1982, Nature 296: 39-42); prokaryotic expression vectors such as the β-lactamase promoter (Villa-Kamaroffet al., 1978, Proc. Natl. Acad. Sci. USA 75:3727-3731), or the tac promoter (DeBoer et al., 1983, Proc. Natl. Acad. Sci. USA 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1: 161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Appropriate protein expression vectors known to those of skill in the art can be used to express the viral proteins. For example, the plasmid pGT-h described in Berg et al., BioTechniques 14:972-978 or pcDNA3 vectors can be used to construct expression vectors for viral proteins.

In a specific embodiment, the protein expression vector comprises a promoter operably linked to a nucleic acid sequence, one or more origins of replication, and, optionally, one or more selectable markers (e.g., an antibiotic resistance gene). In another embodiment, a protein expression vector that is capable of producing bicistronic mRNA may be produced by inserting bicistronic mRNA sequence. Certain internal ribosome entry site (IRES) sequences may be utilized. Preferred IRES elements include, but are not limited to the mammalian BiP IRES and the hepatitis C virus IRES.

Expression vectors containing gene inserts can be identified by three general approaches: (a) nucleic acid hybridization; (b) presence or absence of "marker" gene functions; and (c) expression of inserted sequences. In the first approach, the presence of the viral gene inserted in an expression vector(s) can be detected by nucleic acid hybridization using probes comprising sequences that are homologous to the inserted gene(s). In the second approach, the recombinant vector/host system can be identified and selected based upon the presence or absence of certain "marker" gene functions (e.g., resistance to antibiotics or transformation phenotype) caused by the insertion of the gene(s) in the vector(s). In the third approach, expression vectors can be identified by assaying the gene product expressed. Such assays can be based, for example, on the physical or functional properties of the viral protein in in vitro assay systems, e.g., binding of viral proteins to antibodies.

In a specific embodiment, one or more protein expression vectors encode and express the viral proteins necessary for the formation of RNP complexes. In another embodiment, one or more protein expression vectors encode and express the viral proteins necessary to form viral particles. In yet another embodiment, one or more protein expression vectors encode and express the all of the viral proteins of a particular negative-strand RNA virus.

5.3. Generation of Recombinant Negative Strand RNA Viruses

The present invention provides methods of generating infectious recombinant negative-strand RNA virus by introducing protein expression vectors and vRNA or corresponding cRNA expressing expression vectors into host cells in the absence of helper virus. The present invention also provides methods of generating infectious recombinant negative-strand RNA virus by introducing protein expression vectors and vRNA or corresponding cRNA expressing expression vectors into host cells in the presence of helper virus.

Protein expression vectors and expression vectors directing the expression of vRNAs or corresponding cRNAs can be introduced into host cells using techniques known to those of skill in the art. For example, expression vectors of the invention can be introduced into host cells by employing electroporation, DEAE-dextran, calcium phosphate precipitation, liposomes, microinjection, and microparticle-bombardment (see, e.g., Sambrook et al., Molecular Cloning: A Laboratory Manual, 2 ed., 1989, Cold Spring Harbor Press, Cold Spring Harbor, N.Y.). The expression vectors of the invention may be introduced into host cells simultaneously or sequentially.

In one embodiment, one or more expression vectors directing the expression of vRNA(s) or corresponding cRNA(s) are introduced into host cells prior to the introduction of expression vectors directing the expression of viral proteins. In another embodiment, one or more expression vectors directing the expression of viral proteins are introduced into host cells prior to the introduction of the one or more expression vectors directing the expression of vRNA(s) or corresponding cRNA(s). In accordance with these embodiments, the expression vectors directing the expression of the vRNA(s) or corresponding cRNA(s) may introduced together or separately in different transfections. Further, in accordance with these embodiments, the expression vectors directing the expression of the viral proteins can be introduced together or separately in different transfections.

In another embodiment, one or more expression vectors directing the expression of vRNA(s) or corresponding cRNA(s) and one or more expression vectors directing the expression of viral proteins are introduced into host cells simultaneously. Preferably, all of the expression vectors are introduced into host cells using liposomes.

Appropriate amounts and ratios of the expression vectors for carrying out a method of the invention may be determined by routine experimentation. As guidance, in the case of liposomal transfection or calcium precipitation of plasmids into the host cells, it is envisaged that each plasmid may be employed at a few μgs, e.g., 1 to 10 μg, for example, diluted to a final total DNA concentration of about 0.1 μg/ml prior to mixing with transfection reagent in conventional manner. It may be preferred to use vectors expressing NP and/or RNA-dependent RNA polymerase subunits at a higher concentration than those expressing vRNA segments. One skilled in the art will appreciate that the amounts and ratios of the expression vectors may vary depending upon the host cells.

In one embodiment, at least 0.5 μg, preferably at least 1 μg, at least 2.5 μg, at least 5 μg, at least 8 μg, at least 10 μg, at least 15 μg, at least 20 μg, at least 25 μg or at least 50 μg of one or more protein expression vectors of the invention are introduced into host cells to generate infectious recombinant negative-strand RNA virus. In another embodiment, at least 0.5 μg, preferably at least 1 μg, at least 2.5 μg, at least 5 μg, at least 8 μg, at least 10 μg, at least 15 μg, at least 20 μg, at least 25 μg or at least 50 μg of one or more expression vectors of the invention directing the expression of vRNAs or cRNAs are introduced into host cells to generate infectious recombinant negative-strand RNA virus.

Host cells which may be used to generate the negative-strand RNA viruses of the invention include primary cells, cultured or secondary cells, and transformed or immortalized cells (e.g., 293 cells, 293T cells, CHO cells, Vero cells, PK, MDBK, OMK and MDCK cells). Host cells are preferably animal cells, more preferably mammalian cells, and most preferably human cells. In a preferred embodiment, infectious recombinant negative-strand RNA viruses of the invention are generated in 293T cells.

It is known that Vero cells are deficient in interferon expression (Diaz et al., 1998, Proc. Natl. Acad. Sci. USA 85:5259-5263), which might be a factor in attaining good viral rescue. Hence, it is extrapolated that Vero cells and other cells deficient in interferon activity or response which will support growth of segmented negative-strand RNA viruses may be useful in the practice of the invention.

In order to rescue recombinant influenza B viruses, 293 T cells may not be the most efficient host cell to achieve rescue. Thus, in accordance with the present invention, methods to achieve rescue influenza B virus should utilize host cells which support the efficient replication of influenza B, such as MDCK (canine kidney), PK (porcine kidney) or OMK (owl monkey kidney) cells. Alternatively, MDBK (bovine kidney) cells may be used as hots cells to support rescue of influenza B. Despite the fact that MDBK cells do not support the growth of influenza B, using a reverse genetics approach this cell line supports rescue of influenza B (Barclay et al., 1995, J. Virol. 69:1275-1279).

The present invention provides methods of generating infectious recombinant negative-strand RNA virus in stably transduced host cell lines. The stably transduced host cell lines of the invention may be produced by introducing cDNA controlled by appropriate expression control elements (e.g., promoter, enhancer, sequences, transcription terminators, polyadenylation sites, etc.), and a selectable marker into host cells. Following the introduction of the foreign DNA, the transduced cells may be allowed to grow for 1-2 days in an enriched media, and then are switched to a selective media. The selectable marker confers resistance to the cells and allows the cells to stably integrate the DNA into their chromosomes. Transduced host cells with the DNA stably integrated can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

The infectious recombinant negative-strand RNA viruses generated by methods of the invention which are not attenuated, may attenuated or killed by, for example, classic methods. For example, recombinant negative-strand RNA viruses of the invention may be killed by heat or formalin treatment, so that the virus is not capable of replicating. Recombinant negative-strand RNA viruses of the invention which are not attenuated may be attenuated by, e.g., passage through unnatural hosts to produce progeny viruses which are immunogenic, but not pathogenic.

Attenuated or killed viruses produced in accordance with the invention may subsequently be incorporated into a vaccine composition in conventional manner. Where such a virus has a chimeric vRNA segment as discussed above which encodes a foreign antigen, it may be formulated to achieve vaccination against more than one pathogen simultaneously. Attenuated recombinant viruses produced in accordance with the invention which possess a chimeric vRNA segment may also be designed for other therapeutic uses, e.g., an anti-tumor agent or gene therapy tool, in which case production of the virus will be followed by its incorporation into an appropriate pharmaceutical composition together with a pharmaceutically acceptable carrier or diluent.

Helper virus free rescue in accordance with the invention is particularly favored for generation of reassortant viruses, especially reassortant influenza viruses desired for vaccine use. For example, by means of viral rescue in accordance with the invention the HA and NA vRNA segments of an influenza virus, e.g., influenza A/PR8/34 which is recognized as suitable for human administration, may be readily substituted with the HA and NA vRNA segments of an influenza strain associated with an influenza infection epidemic. Such reassortant influenza viruses may, for example, be used for production of a killed influenza vaccine in conventional manner.

The methods of the present invention may be modified to incorporate aspects of methods known to those skilled in the art, in order to improve efficiency of rescue of infectious viral particles. For example, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoprotein (RNPs) which can be used to transect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in U.S. Pat. No. 5,789,229 issued Aug. 4, 1998; in European Patent Publication EP 0702085A1, published Feb. 20, 1996; in U.S. patent application Ser. No. 09/152,845; in International Patent Publications PCR WO97/12032 published Apr. 3, 1997; WO96/34625 published November. 7, 1996; in European Patent Publication EP-A780475; WO99/02657 published Jan. 21, 1999; WO98/53078 published Nov. 26, 1998; WO98/02530 published Jan. 22, 1998; WO99/15672 published Apr. 1, 1999; WO98/13501 published Apr. 2, 1998; WO97/06720 published Feb. 20, 1997; and EPO 780 47SA1 published Jun. 25, 1997, each of which is incorporated by reference herein in its entirety.

5.4. Segmented Negative-Strand RNA Virus Embodiments

The present invention provides a method for generating in cultured cells infectious viral particles of a segmented negative-strand RNA virus having greater than 3 genomic vRNA segments, for example an influenza virus such as an influenza A virus, said method comprising: (a) providing a first population of cells capable of supporting growth of said virus and having introduced a first set of expression vectors capable of directly expressing in said cells genomic vRNA segments to provide the complete genomic vRNA segments of said virus, or the corresponding cRNAs, in the absence of a helper virus to provide any such RNA segment, said cells also being capable of providing a nucleoprotein and RNA-dependent RNA polymerase whereby RNP complexes containing the genomic vRNA segments of said virus can be formed and said viral particles can be assembled within said cells; and (b) culturing said cells whereby said viral particles are produced.

The present invention also provides a method for generating in cultured cells infectious viral particles of a segmented negative-strand RNA virus, said method comprising: (i) providing a first population of cells which are capable of supporting the growth of said virus and which are modified so as to be capable of providing (a) the genomic vRNAs of said virus in the absence of a helper virus and (b) a nucleoprotein and RNA-dependent RNA polymerase whereby RNA complexes containing said genomic RNAs can be formed and said viral particles can be assembled, said genomic vRNAs being directly expressed in said cells under the control of a human Pol I promoter or functional derivative thereof: and (ii) culturing said cells whereby said viral particles are produced.

The present specification also provides a method for generating in cultured cells infectious viral particles of a segmented negative-strand RNA virus, said method comprising: (i) providing a population of cells which are capable of supporting the growth of said virus and which are modified so as be capable of providing (a) the genomic vRNAs of said virus in the absence of a helper virus and (b) a nucleoprotein and RNA-dependent RNA polymerase whereby RNP complex or complexes containing said genomic vRNAs can be formed and said viral particles can be assembled, said genomic RNAs being directly expressed in said cells under the control of a mammalian Pol I, Pol II or Pol III promoter or a functional derivative thereof, e.g., the truncated human Pol I promoter as previously noted above; and (ii) culturing said cells whereby said viral particles are produced.

In a specific embodiment, an infectious recombinant negative-strand RNA virus having at least 4, preferably at least 5, at least 6, or at least 7 genomic vRNA segments in a host cell using the methods described herein.

In a preferred embodiment, the present invention provides for methods of generating infectious recombinant influenza virus in host cells using expression vectors to express the vRNA segments or corresponding cRNAs and influenza virus proteins, in particular PB1, PB2, PA and NA. In accordance with this embodiment, helper virus may or may not be included to generate the infectious recombinant influenza viruses.

The infectious recombinant influenza viruses of the invention may or may not replicate and produce progeny. Preferably, the infectious recombinant influenza viruses of the invention are attenuated. Attenuated infectious recombinant influenza viruses may, for example, have a mutation in the NS1 gene.

In a preferred embodiment, the infectious recombinant influenza viruses of the invention express heterologous (i.e., non-influenza virus) sequences. In another embodiment, the infectious recombinant influenza viruses of the invention express influenza virus proteins from different influenza strains. In yet another preferred embodiment, the infectious recombinant influenza viruses of the invention express fusion proteins.

5.5. Newcastle Disease Virus Embodiments

A specific embodiment of the present invention is the Applicants' identification of the correct nucleotide sequence of the 5' and 3' termini of the negative-sense genomes RNA of NDV. The nucleotide sequence of the 3' termini of the NDV negative-sense genome RNA of the present invention differs significantly from the NDV 3' termini sequence previously disclosed by Collins et al. in Fundamental Virology 3rd Ed. 1996 by Lippincott-Raven Publishers as shown in FIG. 6. The identification of the correct nucleotide sequence of the NDV 3' termini allows for the first time the engineering of recombinant NDV RNA templates, the expression of the recombinant RNA templates and the rescue of recombinant NDV particles.

Heterologous gene coding sequences flanked by the complement of the viral polymerase binding site/promoter, e.g, the complement of 3'-NDV virus terminus of the present invention, or the complements of both the 3'- and 5'-NDV virus termini may be constructed using techniques known in the art. The resulting RNA templates may be of the negative-polarity and contain appropriate terminal sequences which enable the viral RNA-synthesizing apparatus to recognize the template. Alternatively, positive-polarity RNA templates which contain appropriate terminal sequences which enable the viral RNA-synthesizing apparatus to recognize the template, may also be used. Recombinant DNA molecules containing these hybrid sequences can be cloned and transcribed by a DNA-dependent RNA polymerase, such as bacteriophage T7, T3, or the SP6 polymerase and the like, to produce in vitro and in vivo the recombinant RNA templates which possess the appropriate viral sequences that allow for viral polymerase recognition and activity.

As described above, heterologous sequences can be: 1) antigens that are characteristic of a pathogen; 2) antigens that are characteristic of autoimmune disease; 3) antigens that are characteristic of an allergen; and 4) antigens that are characteristic of a tumor. The heterologous sequences can be introduced into viral nucleic acid sequences by techniques described herein or known to those of skill in the art.

The gene segments coding for the NDV HN, P, NP, M, F, or L proteins may be used for the insertion of heterologous gene products. Insertion of a foreign gene sequence into any of these segments could be accomplished by either a complete replacement of the viral coding region with the foreign gene or by a partial replacement. Complete replacement would probably best be accomplished through the use of PCR-directed mutagenesis. Briefly, PCR-primer A would contain, from the 5' to 3'end: a unique restriction enzyme site, such as a class IIS restriction enzyme site (i.e., a "shifter" enzyme; that recognizes a specific sequence but cleaves the DNA either upstream or downstream of that sequence); a stretch of nucleotides complementary to a region of the NDV gene; and a stretch of nucleotides complementary to the carboxy-teminus coding portion of the foreign gene product. PCR-primer B would contain from the 5' to 3' end: a unique restriction enzyme site; a stretch of nucleotides complementary to a NDV gene; and a stretch of nucleotides corresponding to the 5' coding portion of the foreign gene. After a PCR reaction using these primers with a cloned copy of the foreign gene, the product may be excised and cloned using the unique restriction sites. Digestion with the class IIS enzyme and transcription with the purified phage polymerase would generate an RNA molecule containing the exact untranslated ends of the NDV gene with a foreign gene insertion. In an alternate embodiment, PCR-primed reactions could be used to prepare double-stranded DNA containing the bacteriophage promoter sequence, and the hybrid gene sequence so that RNA templates can be transcribed directly without cloning.

The hemagglutinin and neuraminidase activities of NDV are coded for by a single gene, HN. The HN protein is a major surface glycoprotein of the virus. For a variety of viruses, such as influenza, the hemagglutinin and neuraminidase proteins have been demonstrated to contain a number of antigenic sites. Consequently, this protein is a potential target for the humoral immune response after infection. Therefore, substitution of antigenic sites within HN with a portion of a foreign protein may provide for a vigorous humoral response against this foreign peptide. If a sequence is inserted within the HN molecule and it is expressed on the outside surface of the HN it will be immunogenic. For example, a peptide derived from gp 160 of HIV could be inserted into antigenic site of the H N protein for antigenic presentation by the chimeric virus, resulting in the elicitation of both a humoral immune response. In a different approach, the foreign peptide sequence may be inserted within the antigenic site without deleting any viral sequences. Expression products of such constructs may be useful in vaccines against the foreign antigen, and may indeed circumvent a problem discussed earlier, that of propagation of the recombinant virus in the vaccinated host. An intact HN molecule with a substitution only in antigenic sites may allow for HN function and thus allow for the construction of a viable virus. Therefore, this virus can be grown without the need for additional helper functions. The virus may also be attenuated in other ways to avoid any danger of accidental escape.

Other hybrid constructions may be made to express proteins on the cell surface or enable them to be released from the cell. As a surface glycoprotein, the HN has an amino-terminal cleavable signal sequence necessary for transport to the cell surface, and a carboxy-terminal sequence necessary for membrane anchoring. In order to express an intact foreign protein on the cell surface it may be necessary to use these HN signals to create a hybrid protein. In this case, the fusion protein may be expressed as a separate fusion protein from an additional internal promoter. Alternatively, if only the transport signals are present and the membrane anchoring domain is absent, the protein may be secreted out of the cell.

The recombinant templates prepared as described above can be used in a variety of ways to express the heterologous gene products in appropriate host cells or to create chimeric viruses that express the heterologous gene products. In one embodiment, the recombinant template can be used to transect appropriate host cells, may direct the expression of the heterologous gene product at high levels. Host cell systems which provide for high levels of expression include continuous cell lines that supply viral functions such as cell lines superinfected with NDV, cell lines engineered to complement NDV functions, etc.

In an alternate embodiment of the invention, the recombinant templates may be used to transect cell lines that express a viral polymerase protein in order to achieve expression of the heterologous gene product. To this end, transformed cell lines that express a polymerase protein such as the L protein may be utilized as appropriate host cells. Host cells may be similarly engineered to provide other viral functions or additional functions such as NP or HN.

In another embodiment, a helper virus may provide the RNA polymerase protein utilized by the cells in order to achieve expression of the heterologous gene product.

In yet another embodiment, cells may be transfected with vectors encoding viral proteins such as the NP, P and L proteins. Examples of such vectors are illustrated in FIGS. 2A-2C.

In order to prepare chimeric virus, containing modified NDV virus RNAs or RNA coding for foreign proteins in the plus or minus sense, may be used to transect cells which are also infected with a "parent" NDV virus. Following reassortment, the novel viruses may be isolated and their genomes be identified through hybridization analysis. In additional approaches described herein the production of infectious chimeric virus may be replicated in host cell systems that express an NDV viral polymerase protein (e.g., in virus/host cell expression systems; transformed cell lines engineered to express a polymerase protein, etc.), so that infectious chimeric virus are rescued. In this instance, helper virus need not be utilized since this function is provided by the viral polymerase proteins expressed.

In a particularly desirable approach, cells engineered to express all NDV viral genes may result in the production of infectious chimeric virus which contain the desired genotype; thus eliminating the need for a selection system. Theoretically, one can replace any one of the six genes or part of any one of the six genes of NDV with a foreign sequence. However, a necessary part of this equation is the ability to propagate the defective virus (defective because a normal viral gene product is missing or altered). A number of possible approaches exist to circumvent this problem. In one approach a virus having a mutant protein can be grown in cell lines which are constricted to constitutively express the wild type version of the same protein. By this way, the cell line complements the mutation in the virus. Similar techniques may be used to construct transformed cell lines that constitutively express any of the NDV genes. These cell lines which are made to express the viral protein may be used to complement the defect in the recombinant virus and thereby propagate it. Alternatively, certain natural host range systems may be available to propagate recombinant virus.

A third approach to propagating the recombinant virus may involve co-cultivation with wild-type virus. This could be done by simply taking recombinant virus and co-infecting cells with this and another wild-type virus (preferably a vaccine strain). The wild-type virus should complement for the defective virus gene product and allow growth of both the wild-type and recombinant virus. Alternatively, a helper virus may be used to support propagation of the recombinant virus.

In another approach, synthetic templates may be replicated in cells co-infected with recombinant viruses that express the NDV virus polymerase protein. In fact, this method may be used to rescue recombinant infectious virus in accordance with the invention. To this end, the an NDV polymerase protein may be expressed in any expression vector/host cell system, including but not limited to viral expression vectors (e.g., vaccinia virus, adenovirus, baculovirus, etc.) or cell lines that express a polymerase protein (e.g., see Krystal et al., 1986, Proc. Natl. Acad. Sci. USA 83: 2709-2713). Moreover, infection of host cells expressing all six NDV proteins may result in the production of infectious chimeric virus particles. This system would eliminate the need for a selection system, as all recombinant virus produced would be of the desired genotype.

It should be noted that it may be possible to construct a recombinant virus without altering virus viability. These altered viruses would then be growth competent and would not need helper functions to replicate. For example, alter-

5.6. Purification/Isolation of Recombinant Negative Strand RNA Viruses

The recombinant negative strand RNA viruses of the invention can be isolated or purified using techniques known to those of skill in the art (see, e.g., U.S. Pat. No. 5,948,410 and R. J. Kuchler, "Biochemical Methods in Cell Culture and Virology", Dowden, Hutchinson and Ross, Inc., Stroudsburg, Pa. (1977)). For example, using one isolation method, supernatant from host cells expressing the recombinant negative-strand RNA viruses of the invention are filtered through a depth filter with a nominal pore size of 0.5 micron to remove the cellular debris. Subsequently, the recombinant negative-strand RNA viruses are concentrated and purified by ultrafiltration using a membrane with a molecular weight cut-off. Sucrose is added to the concentrate to a final concentration of 30% (w/v) after which formaldehyde is added to a final concentration of 0.015% (w/v). This mixture is stirred at 2-8° C. for 72 hours. Next the virus concentrate is diluted five-fold with phosphate buffered saline and loaded onto a affinity column containing Amicon Cellufine Sulphate. After removing impurities by washing with phosphate buffered saline the virus is eluted with a solution of 1.5 molar sodium chloride in phosphate buffered saline. The eluate is concentrated and desalted by ultrafiltration using a membrane with a molecular weight cut-off.

In another isolation method, supernatant from host cells expressing the recombinant negative-strand RNA viruses of the invention is subject to centrifugation at a speed which will not pellet the virus (e.g., 2,500 rpm for about 20 minutes). The supernatant may then be further purified by ultrafiltration employing a filter having a pore size that is larger than the viral particles. Preferably, a filter of approximately 0.22 microns is used. Following filtration, the viral particles are collected by polyethylene glycol precipitation followed by centrifugation or, more preferably, by high speed centrifugation at about 70,000 rpm. The viral particles are then resuspended in a small volume of buffer, preferably TNE (10 mM Tris-HCl, 100 mM NaCl, 1 mM EDTA, pH 7.4). A non-ionic detergent may optionally be added to the viral particle suspension to dissolve any contaminants. Although the high speed viral pellet is sufficiently pure to use as a source of viral RNA the viral suspension may optionally be further purified by sucrose density gradient centrifugation.

An "isolated" or "purified" recombinant negative-strand RNA virus is substantially free of cellular material or other contaminating proteins from the cell or tissue source from which the protein is derived, and is substantially free of contaminating viruses (e.g., helper virus). A recombinant negative-strand RNA virus that is substantially free of cellular material includes preparations of the recombinant negative-strand RNA virus is at least 50%, preferably at least 60%, at least 75%, at least 85%, at least 95%, or at least 99% free of heterologous protein (also referred to herein as a "contaminating protein"). A recombinant negative-strand RNA virus that is substantially free of contaminating virus includes preparations of the recombinant negative-strand RNA virus is at least 50%, preferably at least 60%, at least 75%, at least 85%, at least 95%, or at least 99% free of contaminating viruses.

5.7. Assays for the Identification of Recombinant Negative Strand RNA Viruses The production of the recombinant negative-strand RNA viruses of the invention may assessed using any technique known to one of skill in the art. For example, recombinant negative-strand RNA viruses of the invention may be assessed by cell-free reverse transcriptase (hereinafter "RT") activity assay in the cultures and by electron microscopy. Further, any conventional assay which detects virus-specific proteins may be employed to detect the production of the recombinant negative-strand RNA viruses of the invention. Such assays include, for example, Western blots, ELISA, radioimmunoassay, or polyacrylamide gel electrophoresis and comparison to a virus standard.

The production of infectious, replicating recombinant negative-strand RNA viruses of the invention may be assessed using techniques known to those of skill in the art. In particular, the production of infectious, replicating recombinant negative-strand RNA viruses of the invention may be assessed by a plaque assay using, for example, MDCK cells.

5.8. Vaccine Formulations

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Vaccine formulations may include genetically engineered negative strand RNA viruses that have mutations in the NS1 or analogous gene. They may also be formulated using negative strand RNA viruses that have mutations in the NS1 or analogous gene that are natural variants, such as the A/turkey/Ore/71 natural variant of influenza A, or B/201, and AWBY-234, which are natural variants of influenza B. Furthermore, vaccines can include viruses that have mutations in the NS1 or analogous gene resulting from spontaneous mutation events, UV irradiation, exposure to chemical mutagens, or any other genetically-altering event.

Many methods may be used to introduce the vaccine formulations described above, these include but are not limited to oral, intradermal, intramuscular, intraperitoneal, intravenous, subcutaneous, and intranasal routes. It may be preferable to introduce the virus vaccine formulation via the natural route of infection of the pathogen for which the vaccine is designed. Where a live virus vaccine preparation is used, it may be preferable to introduce the formulation via the natural route of infection for influenza virus. The ability of influenza virus to induce a vigorous secretory and cellular immune response can be used advantageously. For example, infection of the respiratory tract by influenza viruses may induce a strong secretory immune response, for example in the urogenital system, with concomitant protection against a particular disease causing agent.

5.9. Pharmaceutical Compositions

The present invention encompasses pharmaceutical compositions comprising recombinant viruses of the invention to be used as anti-viral agents or anti-tumor agents. The pharmaceutical compositions have utility as an anti-viral prophylactic and thus in accordance may be administered to a subject when the subject has been exposed or is expected to be exposed to a virus. For example, in the event that a child comes home from school where he is exposed to several classmates with the flu, a parent would administer the anti-viral pharmaceutical composition of the invention to herself, the child and other family members to prevent viral infection and subsequent illness.

Various delivery systems are known and can be used to administer the pharmaceutical composition of the invention, e.g., encapsulation in liposomes, microparticles, microcapsules, recombinant cells capable of expressing the mutant viruses, receptor-mediated endocytosis (see, e.g., Wu and Wu, 1987, J. Biol. Chem. 262:4429-4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the pharmaceutical composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the pharmaceutical composition can be delivered in a controlled release system. In one embodiment, a pump may be used (see Langer, slipra; Sefton, 1987, CRC Crit. Ref. Biomed. Eng. 14:201; Buchwald et al.,1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, in Medical Applications of Controlled Release, sipra, vol. 2, pp. 115-138 (1984)).

Other controlled release systems are discussed in the review by Langer (Science 249:1527-1533 (1990)).

The pharmaceutical compositions of the present invention comprise a therapeutically effective amount of a mutant virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a henmetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the kit contains a Therapeutic of the invention, e.g., a lats protein, or therapeutically effective lats erivative or analog, or nucleic acid encoding the same, and one or more chemotherapeutic gents.

6. EXAMPLE

Helper Virus Free Rescue of Influenza A/WSN/33

The present invention demonstrates the ability to generate recombinant negative-trand RNA viruses in the absence of helper virus using expression vectors.

Materials & Methods

Preparation of Plasmids Encoding the vRNA Segments of an Influenza A Virus

Eight plasmids (pPOL1-PB2-RT, pPOL1-PB1-RT, pPOL1-PA-RT, pPOL1-HA-RT, pPOL1-NP-RT, pPOL1-NA-RT, pPOL1-M-RT and pPOL1-NS-RT) each expressing a different vRNA segment of influenza A/WSN/33 were constructed. These plasmids are based on the pUC19 or pUC18 plasmids and have a structure analogous to the model vRNA segment encoding plasmid, pPOL1-CAT-RT, described in Pleschka et al., 1996, J. Virol. 70:4183-4192, except that the cDNA encoding the vRNA CAT reporter gene segment (an open reading frame for chloramphenicol acetytransferase in negative polarity flanked by the non-coding regions of the NS-encoding vRNA segment of influenza A/WSN/33) has been substituted by a cDNA encoding a native vRNA segment of influenza A/WSN/33. Each of the plasmids comprise a truncated human RNA Pol I promoter (positions −250 to −1) fused to the end of the vRNA segment encoding cDNA to ensure that the correct 5' end of the transcribed vRNA. Further, each of the vRNA segment encoding plasmids comprise the sequence of the hepatitis delta virus genomic ribozyme to that ensure the correct 3' end of the transcribed vRNA.

Samples of influenza A/WSN/33 for preparation of the cDNA inserts of the above-described plasmids are obtainable, for example, from the W.H.O. Collaborating Centre, Division of Virology, National Institute for Medical research, London, U.K.)

Preparation of Plasmids for Expression of the PB1, PB2, PA and NP Proteins of Influenza A/WSN/33

Four expression plasmids, pGT-h-PB 1, pGT-h-PB2, pGT-h-PA and p-GT-h-NP, encoding the influenza PB1, PB2, PA and NP proteins, respectively, under the control of the adenovirus 2 major late promoter linked to a synthetic sequence comprising the spliced tripartite leader sequence of human adenovirus type 2 were constructed. This promoter has been reported to give high-level expression of proteins in cells adapted to serum-free suspension culture (Berg et al., 1993, BioTechniques 14:972-978). The pGT-h set of protein expression plasmids was constructed by inserting the open reading frames for the PB1, PB2, PA and NP proteins into the Bcl1 cloning site of the pGT-h plasmid (Berg et al., 1993, ibid).

Viral Rescue

Five μg of each of the polymerase protein expression plasmids, 10 μg of the NP-expressing plasmid and 3 μg of each of the 8 vRNA-encoding plasmids were diluted to a concentration of 0.1 μg/μl in 20 mM Hepes buffer (pH 7.5). The DNA solution was added to diluted DOTAP liposomal transfection reagent (Boehringer Mannheim) containing 240 μl of DOTAP and 720 μl of 20 mM Hepes buffer (pH 7.5). The transfection mixture was incubated at room temperature for 15 minutes and then mixed with 6.5 ml of Minimal Essential Medium (MEM) containing 0.5% fetal calf serum (FCS), 0.3% bovine serum albumin (BSA), penicillin and streptomycin. This mixture was added to near-confluent Vero cells in 8.5 cm diameter dishes (about $10^7$ cells covering about 90% of the dish) washed with PBS. After 24 hours, the transfection medium was removed from the cells and replaced with 8 ml of fresh medium (MEM) containing 0.5% FCS, 0.3% BSA, penicillin and streptomycin. The transfected Vero cells were cultured for at least 4 days after transfection. Every day, the medium from the transfected cells was collected and assayed for the presence of influenza virus by plaquing a 0.5 ml aliquot on MDBK cells in conventional manner. The rest of the medium was transferred into 75 $cm^2$ flasks of subconfluent MDBK cells for amplification of any rescued virus. The original transfected cells were further incubated after adding 8 ml of fresh medium.

Introduction of Genetic Tags into 2 vRNA Segments

A cDNA was constructed encoding an HA vRNA segment with a mutation of 6 nucleotides near the 3' end of the segment. Nucleotides 31 to 35 from the 3' end (3'-UUUUG-5') were replaced with 3'-AAAAC-5' resulting in amino acid substitution at amino acid 4(K→F) and at amino acid 5 (L→V) near the N-terminus of HA within the signal peptide. In addition, a silent C→U mutation was created at nucleotide 40. These changes introduced several new restriction sites, including a unique SpeI site. The cDNA encoding the NA segment was mutated to encode an NA segment containing two silent mutations at nucleotides 1358 and 1360 so as to introduce a new unique SacI restriction site (Pleschka et al., 1996, J. Virol. 70:4188-4192). These cDNA were incorporated into the pPOL1 expression vectors described above.

Rescued transfectant virus was generated in Vero cells using the two expression plasmids encoding 2 genetic tags in place of the pPOL1-HA-RT and pPOL1-NA-RT plasmids described above. The rescued virus was amplified in MDCK cells as described above. Medium from MDBK cells infected with the rescued transfectant virus was used to isolate vRNA. One µl of the medium was treated with 5 µl of RNase-free DNase to remove any residual plasmid DNA carried over. After 15 minutes at 37° C., vRNA was isolated using the RNeasy Mini Kit (Qiagen). Short regions of the HA and NA vRNAs expected to contain the genetic tags were amplified by RT-PCR and then analysed by digestion with SpeI and SacI restriction enzymes, respectively. As a control, the same regions of the HA and NA segments were amplified from vRNA isolated from authentic influenza A/WSN/33 virus using the same RT-PCR primers.

RESULTS

The pGT-h-PB1, pGT-h-PB2, pGT-h-PA and p-GT-h-NP expression plasmids encoding the viral nucleoprotein and 3 protein subunits of the viral RNA-dependent RNA polymerase were cotransfected into human 293 cells or Vero cells with the expression plasmid pPOL1-CAT-RT. In both the transfected human 293 cells and Vero cells, CAT activity could be detected (data not shown). Vero cells were chosen for helper virus free generation of influenza A/WSN/33 from transfected vRNA segments since they support better growth of influenza A/WSN/33 than human 293 cells (about one log difference in maximum viral titre).

At early stages post-transfection positive-sense mRNA from the 4 protein expression plasmids coexists with naked negative-sense genomic vRNA transcribed from the transcription plasmids. Thus, double-stranded RNA may form. Formation of such double-stranded RNA in human cells could possibly lead to the induction of interferon-mediated antiviral responses and consequently to suppression of the growth of any rescued virus. However, such interferon-induction is obviated as a problem in Vero cells since such cells are deficient in interferon expression.

To rescue transfectant influenza A/WSN/33 virus, 4 expression plasmids encoding the viral nucleoprotein and 3 protein subunits of the viral RNA-dependent RNA polymerase (pGT-h-PB1, pGT-h-PB2, pGT-h-PA and p-GT-h-NP) and 8 plasmids (pPOL1-PB2-RT, pPOL1-PB1-RT, pPOL1-PA-RT, pPOL1-HA-RT, pPOL1-NP-RT, pPOL1-NA-RT, pPOL1-M-RT and pPOL1-NS-RT) each expressing a different vRNA segment of influenza A/WSN/33 were cotransfected into Vero cells. The culture supernatant from the Vero cells was assessed for rescued transfectant virus by plaque assays using MDCK cells. Four days post-transfection infectious influenza virus was recovered. Approximately 10-20 plaque-forming viral particles were obtained from a 8.5 cm dish containing approximately $10^7$ cells. The rescued virus showed a specific property characteristic of influenza A\WSN/33 virus, i.e., it formed plaques on MDBK cells in the absence of trypsin. The plaques formed by the rescued virus were comparable in size to those formed by a control authentic A/WSN/33 virus sample grown on the same MDBK cells.

To confirm that the viral plaques observed on the MDBK cells treated with virus harvested from the culture medium of transfected cells were derived from the cloned cDNAs, genetic tags were introduced into two of the 8 vRNA segment cDNAs. Isolated vRNA from rescued transfectant virus was used to amplify the genetic tags by RT-PCR. The PCR products obtained from the rescued virus and the control virus were the same size. Those PCR products originating from the HA and NA segments of the rescued virus could be digested with SpeI and SacI, respectively. However, the PCR products corresponding to the control virus were, as expected, not digested by the same enzymes. The omission of reverse transcriptase in control RT-PCR reactions resulted in no visible PCR products.

The results described herein demonstrate that an influenza A virus can be rescued by cotransfecting 8 transcription plasmids for the individual vRNA segments and 4 expression plasmids encoding the required NP, PB1, PB2 and PA proteins into Vero cells in the absence of any helper virus.

It is noted that unlike some of the earlier studies which emphasized the importance of using positive strand RNA for rescuing negative strand RNA viruses, including Bunyamwera virus whose genome is in 3 segments (Schnell et al., 1994, EMBO J. 13:4195-4203; Roberts and Rose, 1998, Virology 247:1-6; and Bridgen and Elliot, 1996, 93:15400-15404), individual negative sense vRNA segments were used herein to generate the recombinant influenza virus.

7. EXAMPLE

Helper Virus Free Rescue OF A/PR/8/34 Influenza (Cambridge Variant)

In order to rescue A/PR/8/34 entirely from recombinant DNA, 12 plasmids were generated. The 12 plasmids are analogous to those described for the rescue of A/WSN/33 virus (see Example 6 above), with a few modifications. The 8 plasmids required for the synthesis of the 8 vRNA segments, by cellular RNA Polymerase I, have a marine rDNA terminator sequence (GenBank Accession. Number M12074) instead of the hepatitis delta virus ribozyme to generate the exact 3' end of the vRNA segments. The 4 protein expression plasmids for the A/PR/8/34 polymerase subunits (PB1, PB1, PA) and the nucleoprotein (NP) are based on the commercially available pcDNA3 (Invitrogen, Catalogue No. V790-20), which has a cytomegalovirus (CMV) promoter and a bovine growth hormone (BGH) poly(A) site.

Construction of the Plasmid pPolISapIT

In order to allow easy cloning of the 8 vRNA segments, a new basic cloning vector, PolISapIT, was constructed. In this new construct, the marine rDNA terminator sequence positions +572 to +715) is positioned downstream of the Pol I promoter. The Pol I promoter and terminator sequences are separated by a 24 bp linker sequence (5'-AGAAGAGCCA-GATCTGGCTCTTCC-3', (SEQ ID NO: 5)) containing SapI restriction sites.

Plasmid pPolISapIT was derived from pPolI-CAT-RT (originally described in Pleschka et al., J. Virol. 70, 4188-4192, 1996). A DNA fragment containing a region of the marine rDNA terminator sequence (positions +335 to +715, GenBank accession number M12074) was inserted into the SalII site of pPolI-CAT-RT to generate pPolI-CAT-T. Subsequently, by using an inverse PCR technique, the CAT gene, the ribozyme and part of the marine rDNA terminator sequence (positions +335 to +571) were deleted from pPolI-CAT-T. At the same time, the 24 bp linker sequence as given above was introduced through the PCR primers between the PolI promoter and the marine rDNA terminator sequence.

Construction of the vRNA Expression Vectors cDNA was generated by RT-PCR from vRNA isolated from influenza A/PR/8/34 virus (Cambridge variant) using PCR primers with SapI overhangs. After SapI digestion, the PCR products were cloned into pPolISapIT digested with SapI.

Viral Rescue

Cotransfection of the 12 plasmids into Vero cells using DOTAP transfection reagent was performed as described in Example 6 (see also Fodor et al., 1999, J. Virol. 73:9679-9682). Plaque assays and viral amplification were performed on MDCK cells in the presence of 0.5 µg/ml trypsin.

Results

Cotransfection of the 12 plasmids described supra resulted in the rescue of infectious influenza A/PR/8/34 particles 4 days posttransfection. These results demonstrate that influenza A/PR8/34 virus can be successfully rescued by the helper virus-free method of the invention. This is of particular interest since influenza A/PR8/34 is known to be avirulent to humans (Beare et al., 1975, Lancet (ii):729-732), whereas influenza A/WSN/33 is considered unsuitable for administration to humans because of its known neurotropism in mice. It is thus proposed that influenza A/PR8/34, in a suitably attenuated form, would be suitable as a parent virus for live vaccine development. For example, helper virus-free viral rescue in accordance with the invention could be used to generate an attenuated reassortant virus starting with expression vectors for the vRNAs of influenza A/PR8/34 apart from substitution of the HA and NA genomic segments of A/PR8/34 virus with the HA and NA genomic segments of an influenza strain associated with an influenza infection epidemic.

8. EXAMPLE

Improved Protocols for the Helper Virus Free Rescue of Influenza A/WSN/33

293T cells were cotransfected with the four protein expression plasmids described in Example 7 and the eight vRNA expression plasmids described in Example 7 (see also Fodor et al., 1999, J. Virol. 73:9679-9682) using in the 3 protocols set out below. These protocols resulted in the production of between 100-10,000 plaque-forming viral particles from $10^6$ cells were obtained on day 2 posttransfection. This is at least 100 times more influenza virus than obtained by the transfection studies reported in Example 6.

Protocol (a): Transfection of 293T Cells Using "LipofectAMINE 2000" Transfection Reagent One µg of each of the 12 plasmids were combined and the volume adjusted to 50 µl by adding OPTIMEM medium (Gibco BRL). In a polystyrene tube, 12 µl of LipofectAMINE 2000 (Gibco BRL, Cat. No. 11 668-027) and 238 µl of OPTIMEM medium were combined and the mixture incubated for 5 minutes at room temperature. The DNA mixture was then added drop-wise into the diluted LipofectAMINE 2000 transfection reagent. After incubating the DNA-Lipofectamine mixture at room temperature for about 20 minutes, the mixture was added drop-wise into a 293T cell suspension (about $10^6$ cells in 1 ml of DMEM containing 10% FCS without antibiotics). At about 16-24 hours post transfection, the transfection mixture was removed and replaced with 1 ml of DMEM containing 0.5% FCS, 0.3% BSA, penicillin and streptomycin. Twenty-four to forty-eight hours later, rescued virus was screened for by plaquing 100 µl of the medium from the transfected 293T cells on MDBK cells and by passaging the rest of the medium on a 25 cm² semiconfluent MDBK flask. One ml of DMEM containing 0.5% FCS, 0.3% BSA penicillin and streptomycin was added to the transfected 293T cells and incubation continued for another 2 to 3 days before repeating the plaquing and amplification on MDBK cells.

Protocol (b): Transfection of 293T Cells Using Calcium Phosphate Precipitation

For transfection using calcium phosphate precipitation, 1 µg of each of the 12 plasmids was combined and the plasmid mixture added to 250 µl 2× HEBS buffer (40 mM Hepes, 280 mM NaCl, 10 mM KCl, 2 mM Na$_2$HPO$_4$, 10 mM glucose, pH 7.05). Then 250 µl of 250 mM CaCl$_2$ was added and the contents of the tube mixed vigorously. After 20-30 mins at room temperature, the precipitate was mixed with 1 ml of DMEM containing 10% FCS, penicillin and streptomycin and added to a 293T cell suspension (about $10^6$ cells in 1 ml of DMEM containing 10% FCS without antibiotics). At about 16-24 hours post transfection, the transfection mixture was removed and replaced with 1 ml of DMEM containing 0.5% FCS, 0.3% BSA, penicillin and streptomycin. 24-48 hours later, rescued virus was screened for as in protocol (a) above.

Protocol (c): Transfection of Vero Cells Using DOTAP Transfection Reagent

One µg of each of the 12 plasmids was combined and the volume adjusted to 120 µl by adding 20 mM hepes (pH 7.5) to give a DNA concentration of about 0.1 µg/µl. The DNA solution was then added to diluted DOTAP transfection reagent (Boehringer) containing 60 µl of DOTAP and 200 µl of 20 mM Hepes (pH 7.5) in a polystyrene tube. After incubation of the DNA-DOTAP mixture at room temperature for about 15-20 minutes, the mixture was added drop-wise into a Vero cell suspension (about $10^6$ cells in 1 ml of MEM containing 10% FCS, penicillin and streptomycin). At about 16-24 hours post transfection, the transfection mixture was removed and replaced with 1 ml of MEM containing 0.5% FCS, 0.3% BSA, penicillin, and streptomycin. Twenty-four to forty-eight hours later, rescued virus was screened for by plaquing 100l of the medium from the transfected Vero cells on MDBK cells and by passaging the rest of the medium on a 25 cm² semiconfluent MDBK flask. One ml of MEM containing 0.5% FCS, 0.3% BSA, penicillin, and streptomycin was added to the transfected Vero cells and incubation continued for another 2 to 3 days before repeating the plaquing and amplification on MDBK cells.

9. EXAMPLE

Helper Virus Free Rescue of Reassortant Influenza Viruses

Plasmid-based rescue in accordance with the invention has been successfully used to generate reassortant influenza viruses. The following reassortant viruses were generated:
(i) A/WSN/33 with the PA segment derived from A/PR/8/34
(ii) A/WSN/33 with the NP segment derived from A/PR/8/34
(iii) A/WSN/33 with the M segment derived from A/PR/8/34
(iv) A/WSN/33 with the PB2 segment derived from A/FPV/Dobson/34

These examples demonstrate the utility of the helper virus free method for isolating reassortants. Reassortant viruses based on A/PR8/34 (or other suitable strains) are required for the production of conventional killed vaccines because they grow to high titre in embryonated chicken eggs—used in the commercial production of killed influenza vaccines. As previously indicated above, an important application of helper virus free viral rescue in accordance with the invention is thus seen to be easier and more direct isolation of reassortant viruses than by the classic method of isolating reassortants from a mixed infection of cells with two live viruses. Importantly, using a method of the invention, the need to screen many potential reassortants before the required one is isolated is obviated.

10. EXAMPLE

Helper Virus Free Rescue of Influenza A/WSN/330N ECR-293 Cells

Rescue of influenza A/WSN/33 has been achieved on EcR-293NP cells, a cell line stably expressing influenza NP, by transfecting 11 plasmids expressing genomic vRNA segments and RNA-dependent RNA polymerase subunits PB1, PB2 and PA.

EcR-293NP cells were derived from the commercially available cell line EcR-293 (Invitrogen, Catalogue No. R650-07) which constitutively expresses the VgEcR and RXR subunits of the ecdysone receptor. Influenza NP expression in such cells is inducible in response to ponasterone A. The same protocol specified in Example 8(a) employing LipofectAMINE 2000 transfection reagent was used except that pcDNA-NP was omitted, since the NP protein for the initial encapsidation of the vRNA segments was provided by the EcR-293NP cells.

11. EXAMPLE

Helper Virus Free Rescue of a Recombinant Influenza Virus Expressing a Foreign Antigen The plasmid pPOL1-E6N 18-2A-NA which is capable of expressing a chimeric vRNA segment based on the NA vRNA segment of influenza A/WSN/33 virus was constructed. The modified vRNA coding sequence was inserted between sequences corresponding to a truncated human Pol I promoter and hepatitis delta virus ribozyme as for preparation of the Pol I-expression plasmids described in Example 6. The resultant chimeric gene contained a long open reading frame (ORF) encoding the first 88 amino acids of the E6 protein of human papillomavirus 18 (HPV 18), followed by 17 amino acids corresponding to the self-cleavage motif of the 2A protease of foot-and-mouth-disease virus (FMDV), followed by the amino acid sequence of the NA of influenza A/WSN/33. The coding region was flanked by the non-coding regions of the NA gene of A/WSN/33 virus. In this way, a chimeric influenza virus gene was generated encoding a polyprotein that undergoes self-cleavage, resulting in the generation of an HPV-derived polypeptide and the NA protein. A similar strategy for the expression of foreign antigens by influenza virus vectors generated by classical RNP-transfection has previously been described (T. Muster and A. Garcia-Sastre, Genetic manipulation of influenza viruses, in Textbook of Influenza, K. G. Nicholson, R. G. Webster & A. J. Hay, eds., pp. 93-106 (1998), Blackwell Science Ltd, Oxford, UK.)

The recombinant influenza virus vector expressing the HPV18-derived antigen was generated by cotransfecting into 293T cells pPOL1-E6N18-2A-NA together with 7 PolI-expression vectors encoding wild-type viral RNAs, i.e., PB2, PB1, PA, HA, NP, M and NS as described in Example 6 and the 4 PolI-expression vectors encoding the PB2, PB1, PA and NP proteins as described in Example 7. The rescued virus had the correct nucleotide sequence as confirmed by sequence analysis of its NA-specific viral RNA.

12. EXAMPLE

Expression and Packaging of a Foreign Gene by Recombinant NDV

The expression of the chloramphenicol transferase gene (CAT) using the NDV minigenome is described. The NDV minigenome was prepared using pNDVCAT, a recombinant plasmid containing the CAT gene. The pNDVCAT plasmid is a pUC19 plasmid containing in sequence: the T7-promoter; the 5'-end of the NDV genomic RNA comprising 191 nucleotides of noncoding NDV RNA sequence; 5 inserted nucleotides (3'CTTAA); the complete coding sequence of the chloramphenicol transferase (CAT) gene in the reversed and complemented order; the 3'-end of the NDV genomic RNA sequence comprising 121 nucleotides of noncoding NDV RNA sequence; a BbsI cloning site and several restriction sites allowing run-off transcription of the template. The pNDVCAT can be transcribed using T7 polymerase to create an RNA with Newcastle disease viral-sense flanking sequences around a CAT gene in reversed orientation.

The length of a paramyxovirus RNA can be a major factor that determines the level of RNA replication, with genome replication being most efficient when the total number of nucleotides is a multiple of six. For NDV, the question of whether this rule of six is critical for replication was examined by generating CAT mini-replicons of varying lengths, differing by one to five nucleotides. Only one construct whose genome was divisible by six was able to induce high CAT activity.

Construction of the Newcastle Disease Virus Minigenome

In order to construct an NDV minigenome, as described supra, the following strategy was used. The 5' terminal sequence of genomic NDV RNA was obtained by RACE (Gibco, BRL) using standard techniques in the art. The template for the RACE reaction was genomic RNA which was purified from NDV virions (strain: California-11914-1944). As illustrated in FIG. 4, this terminal sequence comprised 64 nucleotides of a trailer sequence plus 127 nucleotides of the untranslated region of the L gene. Located adjacent to the 191 viral nucleotide sequence, a 5 nucleotide sequence (3'CCTTAA) was inserted. A CAT gene comprised 667 nucleotides of the CAT open reading frame which was placed between the viral 5' and 3'terminal non-coding regions. In order to obtain the 3' terminal region of the NDV sequence, RT-PCR was used. The template for the RT-PCR reaction was in vitro polyadenylated genomic RNA of NDV. As illustrated in FIG. 3, the 3' terminal region of 121 nucleotides was comprised of 56 nucleotides of the untranslated region of the NP gene plus 65 nucleotides of a leader sequence. The resulting construct of the NDV minigenome is shown in FIG. 2. Nucleotide sequences of 3' and 5' non-coding terminal region shown in FIG. 4.

Construction of the NDV NP, P & L Expression Plasmids

As described in Section 5, the transcription or replication of a negative strand RNA genome requires several protein components to be brought in with the virus, including the L protein, P protein and NP protein. In order to facilitate the expression from the NDV minigenome, the genes encoding each of the L, P and NP proteins were cloned into pTM1 expression vectors as illustrated in FIGS. 3A-C. The pTM1 expression vectors comprises a T7 promoter, several cloning sites for insertion of the gene of interest (L, P or NP), a T7 terminator, a pUC19 origin of replication and an ampicillin resistance gene. In order to construct the expression plasmids, full length DNA of NDV nucleoprotein (NP), phosphoprotein (P) and polymerase (L) were obtained by PCR amplification. These DNAs were cloned into T7 polymerase expression vector pTM1, respectively (FIGS. 3A-C).

RNA Transcription of the NDV Minigenome

RNA transcription from the NDV minigene plasmid was performed with the Ribomax kit (Promega) as specified by the manuscripts. In order to allow run-off transcription, 1 μg of NDV minigenome plasmid (pNDVCAT) was digested with Bbs I. The linearized plasmid was then used as a template of transcription reaction (for 2 hours at 37° C.). In order to remove template DNA, the resulting reaction mixture was treated with RNase-free DNase (for 15 min. at 37° C.) and purified by phenol-chloroform extraction, followed by ethanol precipitation.

Cell Transfections

Cos-1 cells, or 293T cells were grown on 35 mm dishes and infected with the helper virus rVV T7 at a multiplicity of infection (moi) of approximately 1 for 1 hour before transfection. The cells were then transfected with the expression vectors encoding the NP, P and L proteins of NDV. Specifically, transfections were performed with DOTAP (Boehringer Mannheim). Following helper virus infection, cells were transfected with the pTM1-NP (1 μg), pTM1-P (1 μg) and pTM1-L (0.1 μg) for 4 hours. Control transfections, lacking the L protein, were performed on a parallel set of cells with pTM1-NP (1 μg), pTM1-P (1 μg) and mock pTM1-L (0 μg). After the 4 hour incubation period, cells were subjected to RNA transfection with 0.5 μg of the NDV-CAT chimeric (−) RNA (see FIG. 1). Following RNA transfection, cells were allowed to incubate for 18 hours. The cell lysates were subsequently harvested for the CAT assay.

CAT Assays

CAT assays were done according to standard procedures, adapted from Gorman et al., 1982, Mol. Cell. Biol. 2: 1044-1051. The assays contained 10 μl of $^{14}$C chloramphenicol (0.5 μCi; 8.3 nM; NEN), 20 μl of 40 mM acetyl CoA (Boehringer) and 50 μl of cell extracts in 0.25 M Tris buffer (pH 7.5). Incubation times were 16-18 hours.

Results

In each cell line transfected with the NP, P, L expression vectors, and the chimeric NDV-CAT RNA, high levels of expression of CAT was obtained 18 hours post-infection. In addition, control transfected cells lacking the L protein did not express CAT.

Rescue of Infectious NDV Viruses Using RNA Derived from Specific Recombinant DNA The experiments described in the subsections below demonstrate the rescue of infectious NDV using RNA which is derived from specific recombinant DNAs. RNAs corresponding to the chimeric NDV-CAT RNA may be used to show that the 191 nucleotides of the 5' terminal and the 121 nucleotides of the 3' terminal nucleotides of the viral RNAs contain all the signals necessary for transcription, replication and packaging of model NDV RNAs. RNAs containing all the transcriptional units of the NDV genomes can be expressed from transfected plasmids. Thus, this technology allows the engineering of infectious NDV viruses using cDNA clones and site-specific mutagenesis of their genomes. Furthermore, this technology may allow for the construction of infectious chimeric NDV viruses which can be used as efficient vectors for gene expression in tissue culture, animals or man.

13. EXAMPLE

Recombinant Newcastle Disease Virus Containing an HIV Antigen gp160 Epitope Inserted into the NDV Genome In the Example presented herein, a chimeric NDV is constructed to express a heterologous antigen derived from gp160 of HIV. The experiments described in the subsections below demonstrate the use of a recombinant RNA template to generate a chimeric NDV that expresses a HIV gp160-derived peptide within the NDV genome and, further, this chimeric NDV is used to elicit a vertebrate humoral and cell-mediated immune response.

Construction of Plasmid

Recombinant NDV cDNA clones expressing HIV gp160 proteins may be constructed in a number of ways known in the art. For example, as illustrated in FIG. 4, the HIV Env and Gag proteins may be inserted into the NDV in a number of locations. In one example, the Env and Gag proteins are inserted between the M and L genes. In a different example, the Env and Gag proteins are inserted 3' to the NP gene (between the leader sequence and NP). Alternatively, these HIV proteins will be incorporated between the NDV envelope proteins (HN and F) at the 3' end. These protiens may also be inserted into or between any of the NDV genes.

Generation of Infectious Chimeric Virus

Transfection of RNA derived from plasmid comprising a recombinant NDV genome may be transfected into cells such as, for example, COS, 293 MDBK and selection of infectious chimeric virus may be done as previously described. See U.S. Pat. No. 5,166,057, incorporated herein by reference in its entirety. The resulting RNA may be transfected into cells infected with wild type virus by using standard transfection protocol procedures. Posttransfection, the supernatant may be collected and used at different dilutions to infect fresh cells in the presence of NDV antiserum. The supernatant may also be used for plaque assays in the presence of the same antiserum. The rescued virus can then be purified and characterized, and used, for example, in antibody production.

Hemagglutination Inhibition and Virus Neutralization Assays

Hemagglutination inhibition (HI) assays are performed as previously described Palmer et al., 1975, Immunol. Ser. 6:51-52). Monoclonal antibodies (2G9, 4B2, 2F1O, 25-5) are prepared by standard procedures with a human anti-gp120 monoclonal antibody. Ascites fluid containing monoclonal antibodies is treated with receptor-destroying enzyme as previously described (Palmer et al., 1975, Immunol. Ser. 6:51-52).

For virus neutralization assay, cells in 30-mm-diameter dishes are infected virus. After a 1 h adsorption, agar overlay containing antibody at different dilutions is added. The cell monolayer is then stained with 0.1% crystal violet at 72 h postinfection.

Immunization 6 weeks old BALB/c mice are infected either via the aerosol route with the virus, or are immunized intraperitoneally (i.p.) with 10 μg of purified virus. For all booster immunizations, 10 μg of purified virus is administered i.p. Sera is collected 7 days after each immunization.

Radioimmunoassay

The radioimmunoassay is performed as previously described (Zaghouani, H. et al., 1991, Proc. Natl. Acad. Sci. USA 88:5645-6549). Briefly, microtiter plates are coated with 5 ug/ml peptide-BSA conjugate, saturated with 2% BSA in phosphate-buffered saline(PBS) and incubated with various dilution of serum. Bound antibodies are revealed by using $^{125}$I labelled antimouse kappa monoclonal antibody.

Radioimmunoprecipitation

The H9 human T cell line is acutely infected with HIV. Four days postinfection, $5 \times 10^7$ infected cells are labelled with $^{35}$S-cysteine, $^{35}$S-methionine, and $^3$H-isoleucine at $2 \times 10^6$/ml in media containing 100 μCi of each isotope per ml. After 20 h of metabolic labelling, the radioactive virions are pelleted by centrifugation for 1 h at 45,000 rpm. The pellet is then resuspended in 1.0 ml of lysis buffer containing 1% Triton X-100 and 2 mM phenylmethylsulfonyl fluoride (PMSF). Approximately 20 μl of sera or 0.5 μg of monoclonal antibody (in 20 μl PBS) and 175 μl of virion lysate are incubated overnight at 4° C. in 0.5 ml immunoprecipitation buffer containing 0.5% sodium dodecyl sulfate (SDS), 1 mg/ml BSA, 2% Triton X-100, and 50 mM sodium phosphate (pH 7.4). The antigen-antibody complexes are bound to protein A-Sepharose beads, and are analyzed by electrophoresis on a 10% SDS-polyacrylamide gel.

HIV-1 Neutralization Assays

The in vitro neutralization assay are performed as described previously (Nara, P. L. et al., 1987, AIDS Res. Hum. Retroviruses 3:283-302). Briefly, serial twofold dilutions of heat-inactivated serum are incubated for 1 h at room temperature with 150-200 syncytium forming units of HIV virus produced in H9 cells. The virus/serum mixture is incubated for 1 h at 37° C. with 50,000 DEAE-dextran treated CEMss cells (adhered to microplate dishes using poly-L-lysine), or 50,000H9 suspension cells. After virus adsorption, the unbound virus is removed and 200 μl of media is added to each well. Four days postinfection, 50 μl of supernatant media is removed for viral p24$^{gag}$ protein quantitation (Coulter Source, Inc.). The total number of syncytia in CEMss cells is counted five days postinfection. The neutralization titers are calculated by comparison with control wells of virus only, and are expressed as the reciprocal of the highest serum dilution which reduced syncytia numbers by more than 50% or inhibited the p24 synthesis by more than 50%.

Induction of CTL Response

BALB/c mice is immunized with 0.2 ml viral suspension containing $10^7$ PFU of chimeric NDV virus. 7 days later, spleen cells are obtained and restimulated in vitro for 5 days with irradiated spleen cells, alone or coated with immunogenic peptides, in the presence of 10% concanavalin A in the supernatant as previously described (Zaghouani, H. et al., 1992, J. Immunol. 148:3604-3609).

Cytolvsis Assay

The target cells coated with peptides are labeled with Na$_5$$_1$Cr$_4$ (100 μCi/$10^6$ cells) for 1 h at 37° C. After being washed twice, the cells are transferred to V-bottom 96-well plates, the effector cells are added, and incubated at 37° C. in 7% $CO_2$. Four hours later, the supernatant is harvested and counted. The maximum chromium release is determined by incubating the cells with 1% Nonidet P40 detergent. The percentage of specific lysis is calculated according to the following formula: [(cpm samples−cpm spontaneous release)/(cpm maximum release−cpm spontaneous release)]×100.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All references cited herein are incorporated herein by reference in the entirety for all purposes.

What is claimed is:

1. A method for producing influenza virus particles for preparation of a vaccine, comprising:
   growing reassortant influenza viruses to produce virus particles and recovering said produced virus particles, wherein said reassortant influenza viruses are produced in cultured cells in the absence of helper virus by introducing into said cultured cells expression vectors sufficient to produce in said cells the genomic vRNA or antigenomic vRNA (cRNA) segments of said reassortant influenza viruses and producing in said cells a nucleoprotein and an RNA dependent RNA polymerase so that RNP complexes containing the genomic vRNA segments of said reassortant influenza viruses are formed
   wherein said expression vectors encode HA, NA, non-HA and non-NA vRNA segments and wherein the HA and NA vRNA segments are HA and NA vRNA segments of a viral strain different from a strain that contains all of the non-HA and non-NA vRNA segments.

2. The method of claim 1, wherein one or more further expression vectors are employed in said cells to express one or more proteins selected from said nucleoprotein and subunits of a RNA-dependent RNA polymerase.

3. The method of claim 1, wherein a cell line was employed which was capable of expressing one or more of said nucleoprotein and the subunits of a RNA-dependent RNA polymerase.

4. The method of claim 1, wherein said virus is an influenza virus of type A, B or C.

5. The method of claim 1, wherein said cells were selected from Vero cells and other cells which are deficient in interferon activity and capable of supporting growth of said viruses.

6. The method of claim 1, wherein said expression vectors were capable of expressing genomic vRNA segments of said viruses.

7. The method of claim 1, wherein said growing of reassortant influenza viruses to produce virus particles occurs in an egg.

8. The method of claim 1, wherein all the required expression vectors were cotransfected into said cells by use of a liposomal transfection reagent, by calcium phosphate precipitation, or by electroporation.

9. The method of claim 1, wherein each of said expression vectors was a plasmid.

10. The method of claim 2, wherein each of said expression vectors was a plasmid.

11. The method of claim 1, wherein each vRNA segment of said viruses or the corresponding cRNAs was present in a separate expression vector.

12. The method of claim 1, wherein the expression of each vRNA segment or cRNA was under the control of a promoter sequence derived from a mammalian Pol I promoter.

13. The method of claim 12, wherein said promoter sequence was a truncated human Pol I promoter sequence consisting of nucleotides −250 to −1 of the corresponding native promoter or a functional derivative thereof.

14. The method of claim 1, wherein the coding sequence for each vRNA segment or cRNA in said expression vectors was followed by a ribozyme sequence or transcription terminator to ensure a correct 3' end of each said RNA.

15. The method of claim 2, wherein expression of one or more viral proteins from said further expression vectors was under the control of a regulatory sequence selected from the adenovirus 2 major late promoter linked to the spliced tripartite leader sequence of human adenovirus type 2 or the human cytomegalovirus immediate-early promoter, or a functional derivative of said regulatory sequence.

16. A method for producing influenza virus particles comprising producing in a cell all of the genomic RNA of an influenza virus by expressing from DNA introduced into the cell at least one or more of genomic RNA or cRNA of the influenza virus and producing in the cell RNA dependent RNA polymerase and nucleoprotein and assembling in the cell the influenza virus, said cell being free of helper virus, wherein said cell is selected from Vero cells and other cells which are deficient in interferon activity and capable of supporting growth of said virus.

17. The method of claim 16, wherein said virus is an influenza virus of type A, B or C.

18. The method of claim 1, wherein said reassortant influenza viruses are at least 99% free from contaminating viruses.

19. A method for producing influenza virus particles for preparation of a vaccine, comprising:
    growing a reassortant influenza virus to produce virus particles and recovering said produced virus particles, wherein said reassortant influenza virus is produced in cultured cells in the absence of helper virus by introducing into said cultured cells expression vectors to produce in said cells the genomic vRNA or antigenomic vRNA (cRNA) segments of a reassortant influenza virus and producing in said cells a nucleoprotein and an RNA dependent RNA polymerase so that RNP complexes containing the genomic vRNA segments of said reassortant influenza virus are formed,
    wherein said expression vectors encode at least 4 different vRNA (or cRNA) segments and wherein each said different vRNA segment is from a single influenza virus strain, wherein all said different vRNA segments are not from the same influenza virus strain, wherein said different vRNA segments include an HA and an NA vRNA segment both of which are from the same influenza virus strain, and wherein said different vRNA segments are selected from PB2, PRI, PA, HA, NP, NA, M and NS.

20. The method of claim 19, wherein said expression vectors encode at least 5 different vRNA segments.

21. The method of claim 19, wherein said expression vectors encode at least 6 different vRNA segments.

22. The method of claim 19, wherein said expression vectors encode at least 7 different vRNA segments.

23. The method of claim 19, wherein said expression vectors encode 8 different vRNA segments.

24. The method of claim 19, wherein all of said different vRNA segments other than HA and NA are from the same influenza virus strain.

* * * * *

UNITED STATES PATENT AND TRADEMARK OFFICE
CERTIFICATE OF CORRECTION

PATENT NO.        : 7,384,774 B2
APPLICATION NO. : 10/652912
DATED             : June 10, 2008
INVENTOR(S)       : Peter Palese et al.

It is certified that error appears in the above-identified patent and that said Letters Patent is hereby corrected as shown below:

In the Specification:

At column 10, line 26, delete "p.m. Howley" and insert thereof --P.M. Howley--

At column 13, line 34, delete "vectors" and insert therefor --vector--

At column 15, line 28, delete "PolI" and insert therefor --Pol I--

At column 16, line 67, delete "an" and insert therefor --a--

At column 26, line 53, delete "an"

At column 29, line 40, delete "in a preferred embodiment"

At column 29, line 67, delete "slipra" and insert therefor --supra--

At column 30, line 16, delete "sipra" and insert therefor --supra--

At column 31, line 49, delete "erivative" and insert therefor --derivative--

At column 31, line 57, delete "trand" and insert therefor --strand--

At column 34, line 5, delete "AIWSN/33" and insert therefor --A/WSN/33--

At column 35, line 7, delete "Sal II" and insert therefor --Sal I--

At column 37, line 32, delete "A/WSN/330N" and insert therefor --A/WSN/33 ON--

At column 38, line 31, delete "plasmidis" and insert therefor --plasmid is--

At column 40, line 52, delete "protiens" and insert therefor --proteins--

At column 42, line 10, delete "50,000H9" and insert --50,000 H9--

UNITED STATES PATENT AND TRADEMARK OFFICE
CERTIFICATE OF CORRECTION

PATENT NO. : 7,384,774 B2
APPLICATION NO. : 10/652912
DATED : June 10, 2008
INVENTOR(S) : Peter Palese et al.

It is certified that error appears in the above-identified patent and that said Letters Patent is hereby corrected as shown below:

In the Claims:

At column 46, line 34 (in claim 19), delete "PRI" and insert therefor --PB1--

Signed and Sealed this

Ninth Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,384,774 B2  Page 1 of 1
APPLICATION NO. : 10/652912
DATED : June 10, 2008
INVENTOR(S) : Peter Palese et al.

It is certified that error appears in the above-identified patent and that said Letters Patent is hereby corrected as shown below:

In the Specification:
At column 1, after line 7, insert:

--GOVERNMENT SUPPORT

This invention was made, in whole or in part, with government support under grant numbers 97308MI and 73054MI awarded by the National Institutes of Health. The Government has certain rights in these inventions.--

Signed and Sealed this
Eighth Day of May, 2012

David J. Kappos
*Director of the United States Patent and Trademark Office*